United States Patent
Dorsey et al.

[11] Patent Number: 6,011,038
[45] Date of Patent: Jan. 4, 2000

[54] PYRAZINONE THROMBIN INHIBITORS

[75] Inventors: Bruce D. Dorsey, Maple Glen; Philip E. Sanderson, Philadelphia; Terry A. Lyle, Lederach, all of Pa.

[73] Assignee: Merck & Co., Inc., Rahway, N.J.

[21] Appl. No.: 09/146,650

[22] Filed: Sep. 3, 1998

Related U.S. Application Data

[60] Provisional application No. 60/058,058, Sep. 5, 1997.

[51] Int. Cl.[7] .................. A61K 31/495; C07D 401/12; C07D 403/12; C07D 413/12
[52] U.S. Cl. .................. 514/252; 514/253; 514/255; 544/405; 544/408
[58] Field of Search .................. 544/405, 408; 514/252, 253, 255

[56] References Cited

U.S. PATENT DOCUMENTS

| | | | |
|---|---|---|---|
| 5,260,307 | 11/1993 | Ackermann et al. | 514/323 |
| 5,405,854 | 4/1995 | Ackermann et al. | 514/315 |
| 5,459,142 | 10/1995 | Tone et al. | 514/252 |
| 5,510,369 | 4/1996 | Lumma et al. | 514/422 |
| 5,744,486 | 4/1998 | Sanderson et al. | 514/318 |
| 5,866,573 | 2/1999 | Sanderson et al. | 514/235.8 |

FOREIGN PATENT DOCUMENTS

| | | |
|---|---|---|
| 262096 | 9/1987 | European Pat. Off. . |
| 509769 | 4/1992 | European Pat. Off. . |
| WO 94/25051 | 11/1994 | WIPO . |
| WO 96/11697 | 4/1996 | WIPO . |
| WO 96/31504 | 10/1996 | WIPO . |
| WO 96/32110 | 10/1996 | WIPO . |
| WO 97/01338 | 1/1997 | WIPO . |
| WO 97/40024 | 10/1997 | WIPO . |

OTHER PUBLICATIONS

Hirsh et al., Chest, vol. 114, pp. 489S–504S, 1998.
Sanderson, P.E., et al., "Preparation of 3–amino–2–pyrazinone–1–acetamide derivatives as thrombin inhibitors," Chem. Abstr., vol. 128, No. 3, p. 532, (1998).
Peter R. Bernstein, et al., "Nonpeptidic Inhibitors of Human Leukocyte Elastase . . . " J. Med. Chem., vol. 37, 1994, pp. 3313–3326.

*Primary Examiner*—Emily Bernhardt
*Attorney, Agent, or Firm*—Richard S. Parr; Melvin Winokur

[57] ABSTRACT

Compounds of the invention are useful in inhibiting thrombin and associated thrombotic occlusions having the following structure:

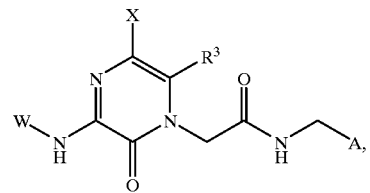

for example:

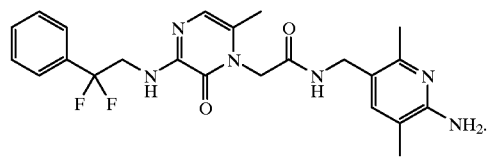

15 Claims, No Drawings

PYRAZINONE THROMBIN INHIBITORS

CROSS-REFERENCE TO RELATED APPLICATIONS

This patent application claims the benefit of U.S. provisional patent application Ser. No. 60/058,058, filed Sep. 5,1997.

BACKGROUND OF THE INVENTION

Thrombin is a serine protease present in blood plasma in the form of a precursor, prothrombin. Thrombin plays a central role in the mechanism of blood coagulation by converting the solution plasma protein, fibrinogen, into insoluble fibrin.

Edwards et al., *J. Amer. Chem. Soc.*, (1992) vol. 114, pp. 1854–63, describes peptidyl a-ketobenzoxazoles which are reversible inhibitors of the serine proteases human leukocyte elastase and porcine pancreatic elastase.

European Publication 363 284 describes analogs of peptidase substrates in which the nitrogen atom of the scissile amide group of the substrate peptide has been replaced by hydrogen or a substituted carbonyl moiety.

Australian Publication 86245677 also describes peptidase inhibitors having an activated electrophilic ketone moiety such as fluoromethylene ketone or a-keto carboxyl derivatives.

R. J. Brown et al., *J. Med. Chem.*, Vol. 37, pages 1259–1261 (1994) describes orally active, non-peptidic inhibitors of human leukocyte elastase which contain trifluoromethylketone and pyridinone moieties.

H. Mack et al., *J. Enzyme Inhibition*, Vol. 9, pages 73–86 (1995) describes rigid amidino-phenylalanine thrombin inhibitors which contain a pyridinone moiety as a central core structure.

SUMMARY OF THE INVENTION

The invention includes compounds for inhibiting loss of blood platelets, inhibiting formation of blood platelet aggregates, inhibiting formation of fibrin, inhibiting thrombus formation, and inhibiting embolus formation in a mammal, comprising a compound of the invention in a pharmaceutically acceptable carrier. These compounds may optionally include anticoagulants, antiplatelet agents, and thrombolytic agents. The compounds can be added to blood, blood products, or mammalian organs in order to effect the desired inhibitions.

The invention also includes a compound for preventing or treating unstable angina, refractory angina, myocardial infarction, transient ischemic attacks, atrial fibrillation, thrombotic stroke, embolic stroke, deep vein thrombosis, disseminated intravascular coagulation, ocular build up of fibrin, and reocclusion or restenosis of recanalized vessels, in a mammal, comprising a compound of the invention in a pharmaceutically acceptable carrier. These compounds may optionally include anticoagulants, antiplatelet agents, and thrombolytic agents.

The invention also includes a method for reducing the thrombogenicity of a surface in a mammal by attaching to the surface, either covalently or noncovalently, a compound of the invention.

DETAILED DESCRIPTION OF THE INVENTION AND PREFERRED EMBODIMENTS

Compounds of the invention are useful as thrombin inhibitors and have therapeutic value in for example, preventing coronary artery disease, and have the following structure:

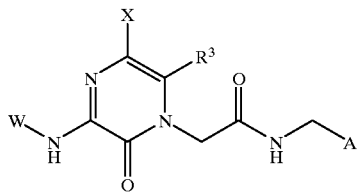

wherein
W is
  hydrogen,
  $R^1$,
  $R^1OCO$,
  $R^1CO$,
  $R^1(CH_2)_nNHCO$, or
  $(R^1)_2CH(CH_2)_nNHCO$,
    wherein n is 0–4;
$R^1$ is
  $R^2$,
  $R^2(CH_2)_mC(R^{12})_2$, where m is 0–3, and each $R^{12}$ can be the same or different,
  $(R^2)(OR^2)CH(CH_2)_p$, where p is 1–4,

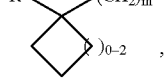

where m is 0–3,

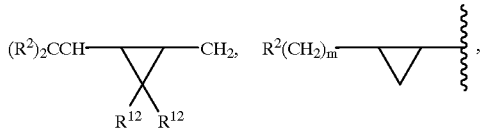

where m is 0 or 1,
$R^2CCCH_2$,
$R^2C(R^{12})_2(CH_2)_m$, wherein m is 0–3, and each $R^{12}$ can be the same or different, wherein $(R^{12})_2$ can also form a ring with C represented by $C_{3-7}$ cycloalkyl,
$R^2CH_2C(R^{12})_2(CH_2)_q$, wherein q is 0–2, and each $R^{12}$ can be the same or different, wherein $(R^{12})_2$ can also form a ring with C represented by $C_{3-7}$ cycloalkyl,
$(R^2)_2CH(CH_2)_r$, where r is 0–4 and each $R^2$ can be the same or different, and wherein $(R^2)_2$ can also form a ring with CH represented by $C_{3-7}$ cycloalkyl, $C_{7-12}$ bicylic alkyl, $C_{10-16}$ tricylic alkyl, or a 5- to 7- membered mono- or bicyclic heterocyclic ring which can be saturated or unsaturated, and which contains from one to three heteroatoms selected from the group consisting of N, O and S,
$R^2O(CH_2)_p$, wherein p is 1–4,
$R^2CF_2C(R^{12})_2$,
$(R^2CH_2)(R^2CH_2)CH$, or
$R^2(COOR^3)(CH_2)r$, where r is 1–4;
$R^2$ and $R^{14}$ are independently
  phenyl, unsubstituted or substituted with one or more of $C_{1-4}$ alkyl, $C_{1-4}$ alkoxy, halogen, hydroxy, COOH, CONH$_2$, CH$_2$OH, CO$_2$R', where R' is C$_{1-4}$ alkyl, or SO$_2$NH$_2$,
naphthyl,
biphenyl,
a 5- to 7- membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen, C$_{1-4}$ alkyl, or hydroxy,
C$_{1-7}$ alkyl, unsubstituted or substituted with one or more of
  hydroxy,
  COOH,
  halogen,
  amino,
  aryl,
  C$_{3-7}$ cycloalkyl,
  CF$_3$,
  N(CH$_3$)$_2$,
  —C$_{1-3}$alkylaryl,
  heteroaryl, or
  heterocycloalkyl,
CF$_3$
C$_{3-7}$ cycloalkyl, unsubstituted, monosubstituted with halogen or aryl, or disubstituted with halogen,
C$_{7-12}$ bicyclic alkyl, or
C$_{10-16}$ tricyclic alkyl;
R$^3$ is
  hydrogen,
  C$_{1-4}$ alkyl,
  C$_{3-7}$ cycloalkyl, or
  trifluoromethyl;
X is hydrogen or halogen;
A is chosen from one of the following radicals:

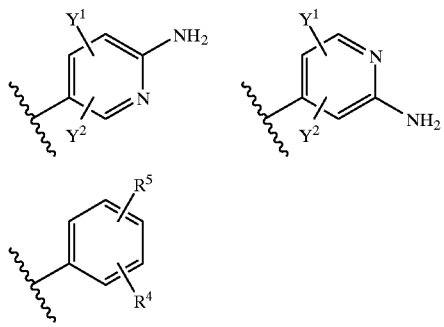

wherein Y$^1$ and Y$^2$ are independently
hydrogen,
C$_{1-4}$ alkyl,
C$_{1-4}$ alkoxy,
C$_{3-7}$ cycloalkyl,
halogen, or
trifluoromethyl;
R$^4$ is
  hydrogen,
  C$_{1-4}$ alkyl,
  C$_{1-4}$ alkoxy,
  halogen,
  —OCH$_2$CF$_3$,
  —OCH$_2$CN,
  —COOH,
  —OH,
  —COOR$^6$, where R$^6$ is C$_{1-4}$alkyl,
  —CONR$^7$R$^8$, where R$^7$ and R$^8$ are independently hydrogen or C$_{1-4}$alkyl,
  —(CH$_2$)$_{1-4}$OH,
  —CH$_2$NHC(O)CH$_3$,
  —CH$_2$NHC(O)CF$_3$,
  —CH$_2$NHSO$_2$CH$_3$,
  —SO$_2$NH$_2$,
  —(CH$_2$)$_{1-4}$SO$_2$NR$^7$R$^8$,
  —(CH$_2$)$_{1-4}$SO$_2$R$^6$,
  a 5- to 7- membered mono- or a 9- to 10-membered bicyclic heterocyclic ring which can be saturated or unsaturated, and which contains from one to four heteroatoms selected from the group consisting of N, O and S,
  —ZCH$_2$CO$_2$H,
  —ZCH$_2$CO$_2$CH$_3$,
  —ZCH$_2$R$^{14}$,
  —ZCH$_2$NHR$^{14}$,
  —ZCH$_2$CO$_2$(CH$_2$)$_{1-3}$CH$_3$,
  —Z(CHR$^9$)$_{1-3}$C(O)NR$^{10}$R$^{11}$,
  wherein
    R$^9$ is H or C$_{1-4}$ alkyl,
    R$^{10}$ and R$^{11}$ are independently
      hydrogen,
      C$_{3-7}$ cycloalkyl,
      aryl,
      heteroaryl,
      heterocycloalkyl,
      —(CH$_2$)$_{1-2}$NCH$_2$CH$_3$,
      C$_{1-4}$ alkyl unsubstituted or substituted with one or more of:
        hydroxy,
        COOH,
        amino,
        aryl,
        heteroaryl, or
        heterocycloalkyl, or
      R$^{10}$ and R$^{11}$ are joined to form a four to seven membered cycloalkyl or heterocycloalkyl ring unsubstituted or substituted with hydroxy, amino or aryl or disubstituted with hydroxy,
      wherein Z is O, S or CH$_2$;
R$^5$ is
  hydrogen,
  halogen,
  C$_{1-4}$ alkyl,
  C$_{1-4}$ alkoxy,
  CF$_3$,
  CN, or
  CO$_2$NH$_2$; and
R$^{12}$ is
  hydrogen,
  phenyl, unsubstituted or substituted with one or more of C$_{1-4}$ alkyl, C$_{1-4}$ alkoxy, halogen, hydroxy, COOH, CONH$_2$,
  naphthyl,
  biphenyl,
  a 5- to 7- membered mono- or a 9- to 10-membered bicyclic heterocyclic ring which can be saturated or unsaturated, and which contains from one to four heteroatoms selected from the group consisting of N, O and S,
  C$_{1-4}$ alkyl, unsubstituted or substituted with one or more of
    hydroxy COOH,
amino,
aryl,
heteroaryl, or
heterocycloalkyl,
$CF_3$,
$C_{3-7}$ cycloalkyl,
$C_{7-12}$ bicyclic alkyl, or
$C_{10-16}$ tricyclic alkyl;
or a pharmaceutically acceptable salt thereof;

In one class of compounds and pharmaceutically acceptable salts thereof, $R^3$ is $C_{1-4}$ alkyl and X is H.

In a subclass of this class of compounds and pharmaceutically acceptable salts thereof, A is i)

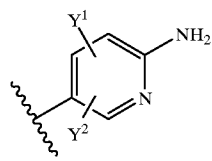

wherein $Y^1$ and $Y^2$ are independently hydrogen, halogen or $C_{1-4}$ alkyl;
or ii)

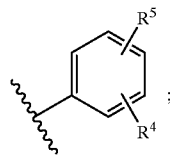

$R^4$ is
hydrogen,
$C_{1-4}$ alkyl,
$C_{14}$ alkoxy,
halogen,
—OH,
—$OCH_2R^{14}$,
—$OCH_2NHR^{14}$,
—$O(CH_2)_{1-3}C(O)NR^{10}R^{11}$,
  wherein
    $R^{10}$ and $R^{11}$ are independently
      hydrogen,
      $C_{3-7}$ cycloalkyl,
      heteroaryl,
      heterocycloalkyl,
      $C_{1-4}$ alkyl substituted with amino, or
    $R^{10}$ and $R^{11}$ are joined to form a four to seven membered cycloalkyl or heterocycloalkyl ring unsubstituted or substituted with hydroxy, amino or aryl or disubstituted with hydroxy,
$R^5$ is
  hydrogen,
  halogen,
  C1–4 alkyl, or
  CN.

In a group of this subclass of compounds and pharmaceutically acceptable salts thereof, W is $R^1$.

In a subgroup of this group of compounds and pharmaceutically acceptable salts thereof,
  $R^1$ is
  $R^2$,
  $R^2(CH_2)_mC(R^{12})_2$, where m is 0–3, and each $R^{12}$ can be the same or different, wherein $(R^{12})_2$ can also form a ring with C represented by $C_{3-7}$ cycloalkyl,
  $R^2C(R^{12})_2(CH_2)_m$, wherein m is 0–3, and each $R^{12}$ can be the same or different, wherein $(R^{12})_2$ can also form a ring with C represented by $C_{3-7}$ cycloalkyl,

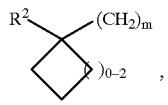

where m is 0–3,

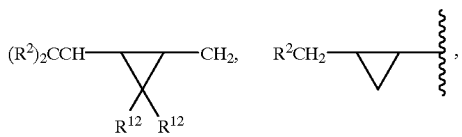

where m is 0 or 1,
  $(R^2)_2CH(CH_2)_{1-2}$, where each $R^2$ can be the same or different,
  $R^2CCCH_2$,
  $R^2CF_2C(R^{12})_2$, or
  $(R^2CH_2)(R^2CH_2)CH$;
$R^2$ is
  phenyl, unsubstituted or substituted with one or more of $C_{1-4}$ alkyl, $C_{1-4}$ alkoxy, halogen, hydroxy, or $SO_2NH_2$,
  a 5- to 7- membered mono- or a 9- to 10-membered bicyclic heterocyclic ring or non-heterocyclic ring which can be saturated or unsaturated, wherein the heterocyclic ring contains from one to four heteroatoms selected from the group consisting of N, O and S, and wherein the heterocyclic or non-heterocyclic ring is unsubstituted or substituted with halogen, $C_{1-4}$ alkyl or hydroxy,
  $C_{3-7}$ cycloalkyl, unsubstituted, monosubstituted or disubstituted with halogen,
  $CF_3$, or
  $C_{1-7}$ alkyl, unsubstituted or substituted with halogen or $C_{3-7}$ cycloalkyl; and
$R^{12}$ is
  hydrogen,
  $C_{1-4}$ alkyl, unsubstituted or substituted with one or more of
    hydroxy,
    COOH,
    amino,
    aryl,
    heteroaryl,
    heterocycloalkyl, or
    halogen.

In a family of this subgroup of compounds and pharmaceutically acceptable salts thereof, A is
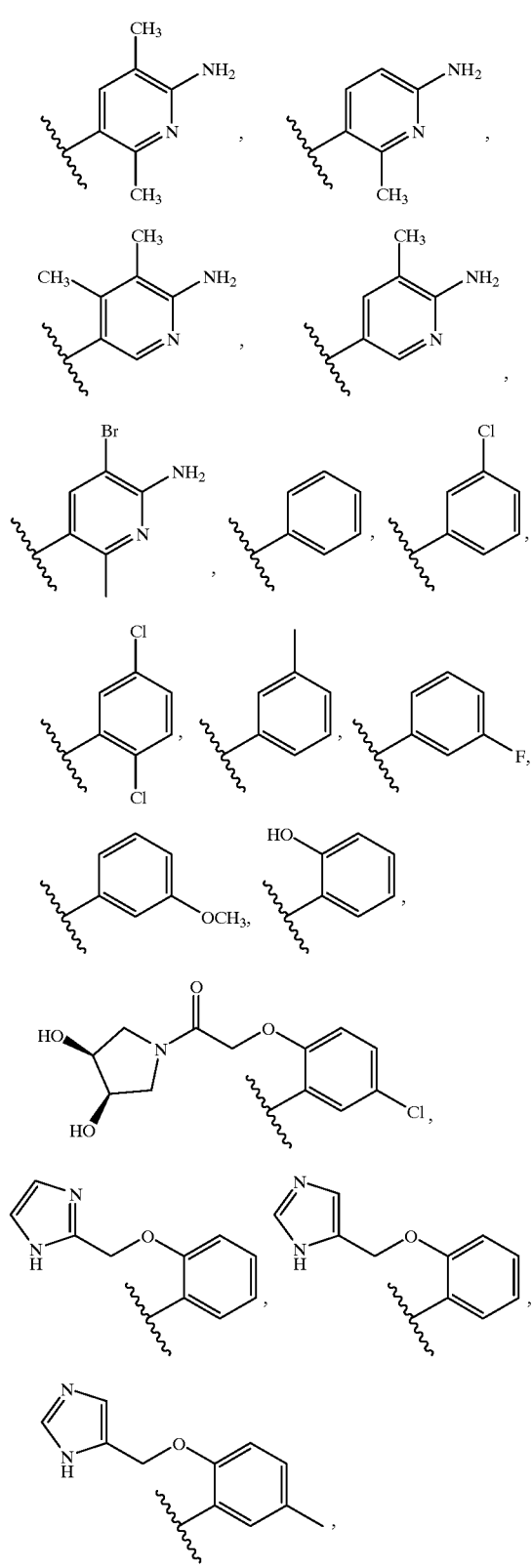
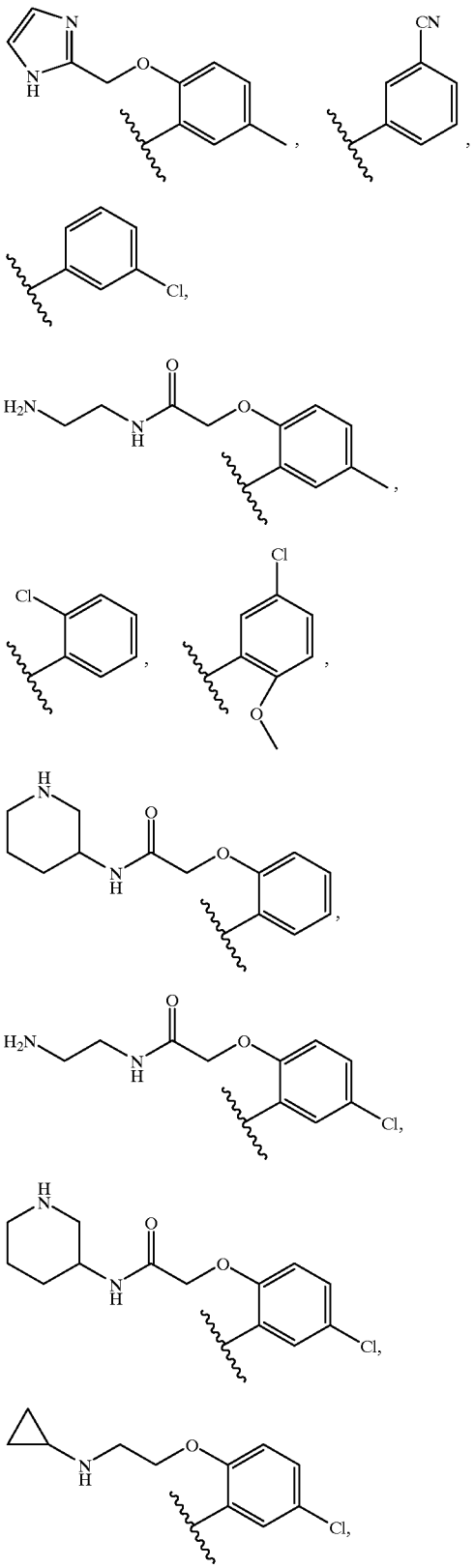

-continued

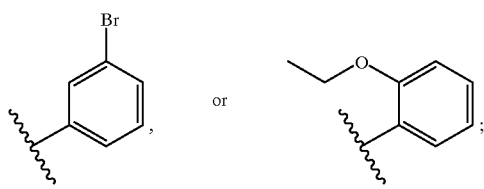

R³ is CH₃, or CH₂CH₃; and
W is PhCH₂CH₂,

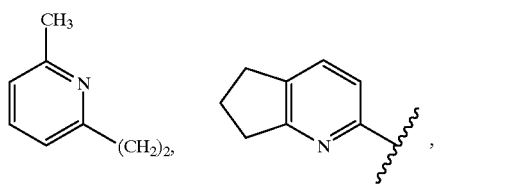

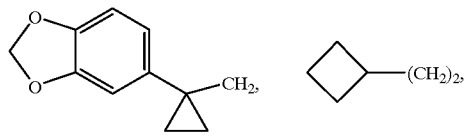

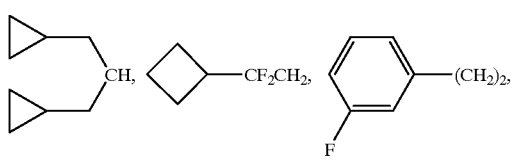

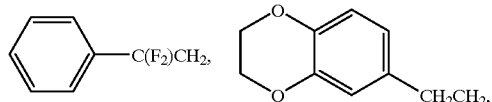

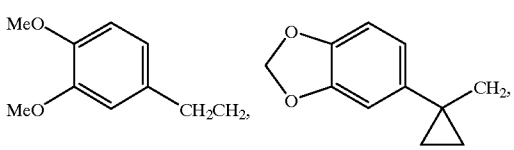

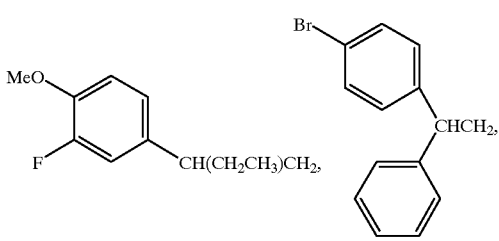

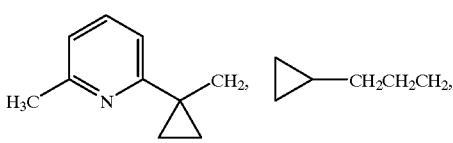

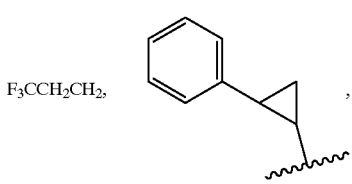

-continued

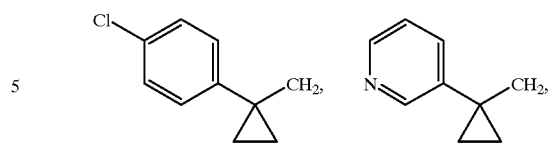

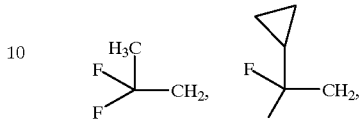

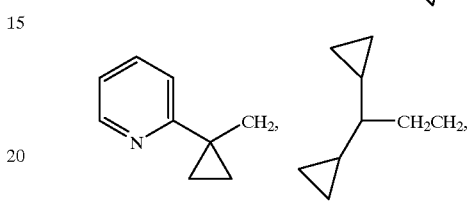

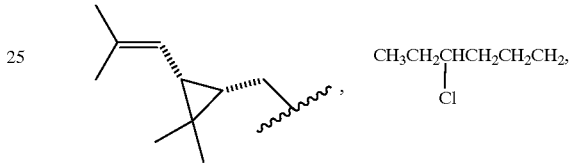

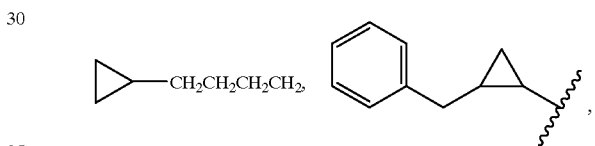

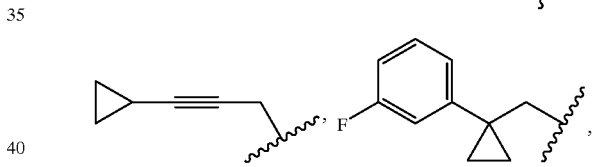

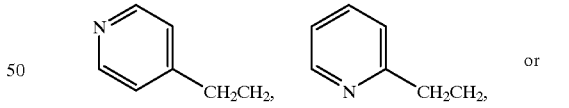

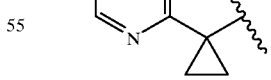

Examples of this family are listed below (note that methyl substituents are conventionally indicated as bonds attached to an atom). Inhibitory activity of compounds of the invention is represented by "*", indicating Ki greater than or equal to 1 nM, or "**", indicating Ki less than 1 nM. Values are as determined according to the in vitro assay described later in the specification.

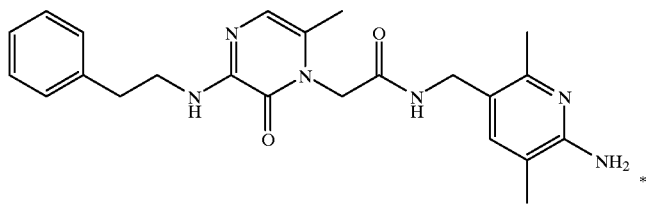 *
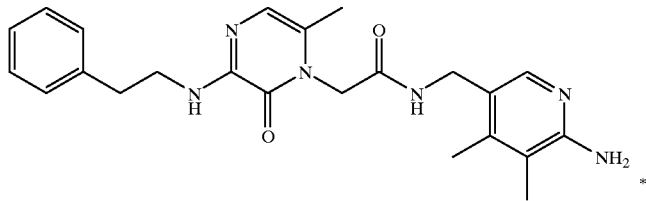 *
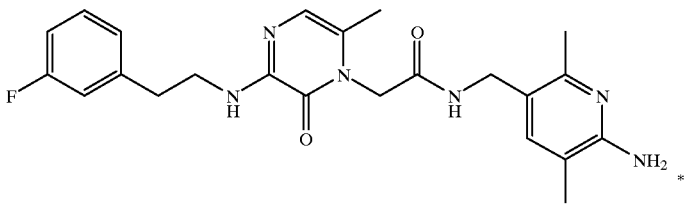 *
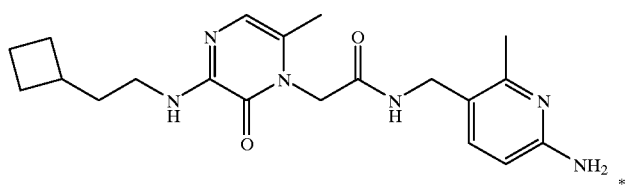 *
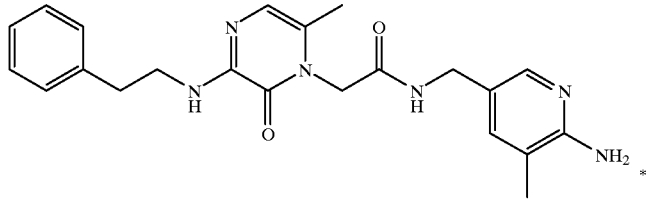 *
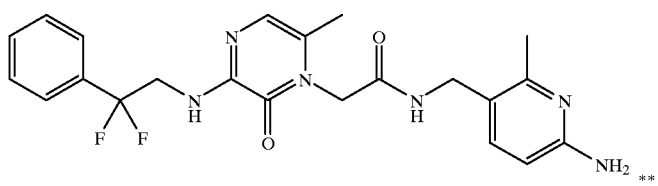 **
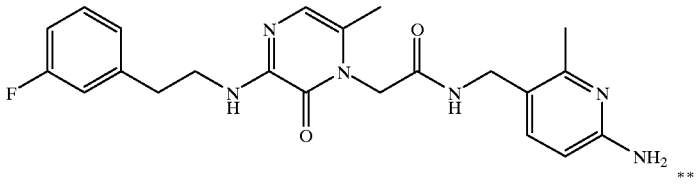 **
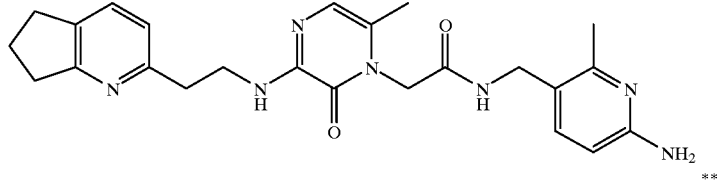 **

-continued
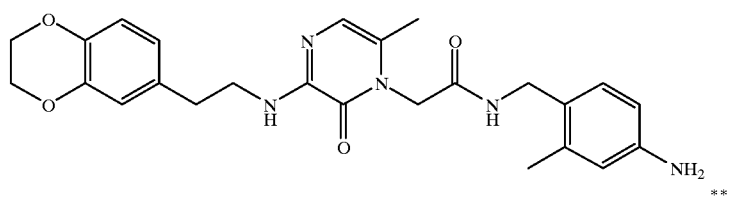
**
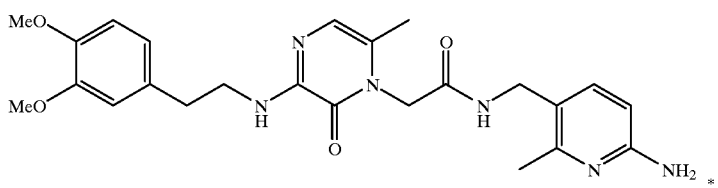
*
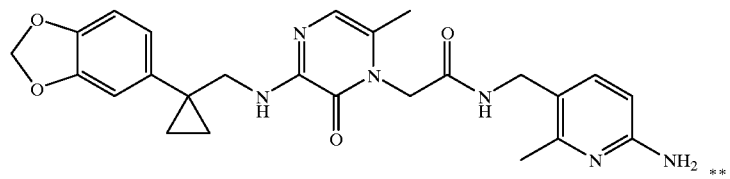
**
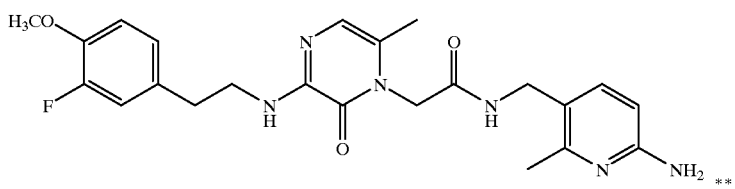
**
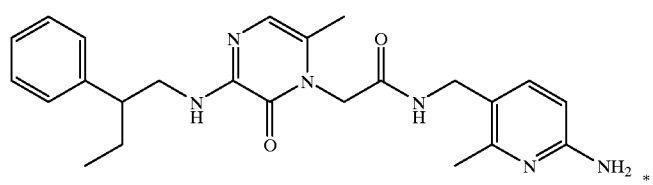
*
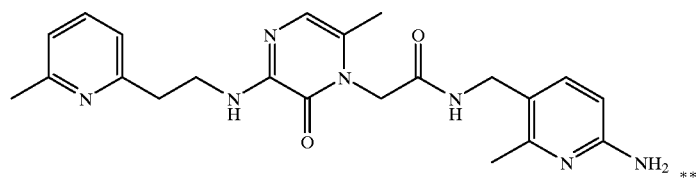
**
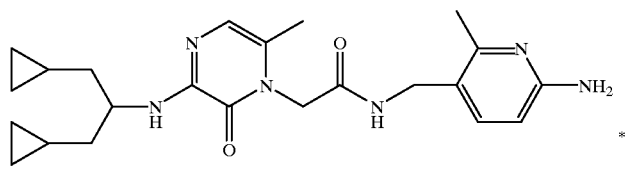
*
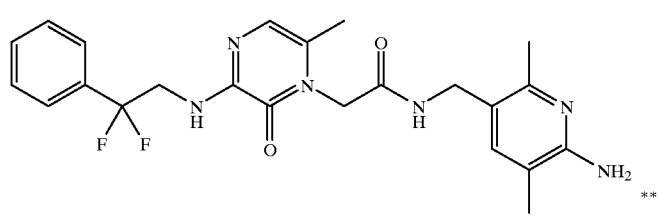
**
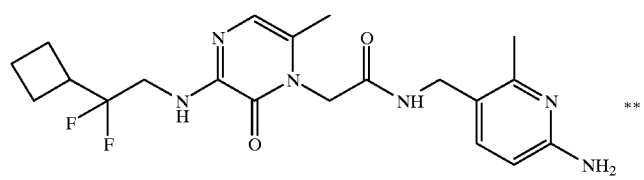
**

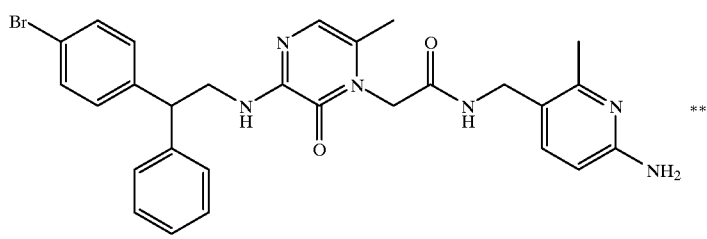 **
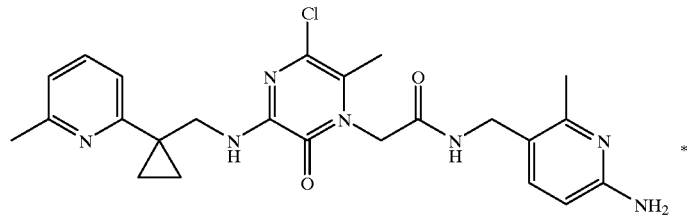 *
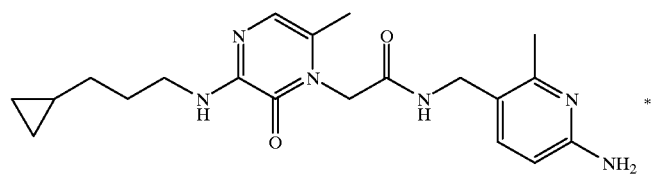 *
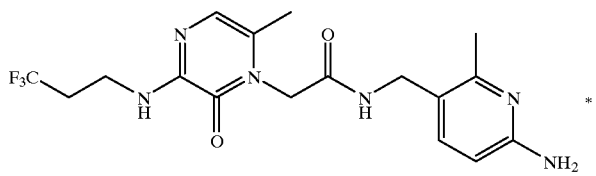 *
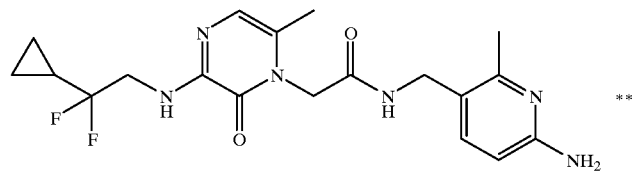 **
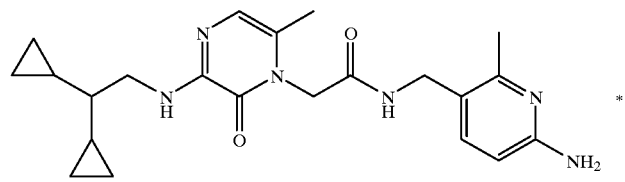 *
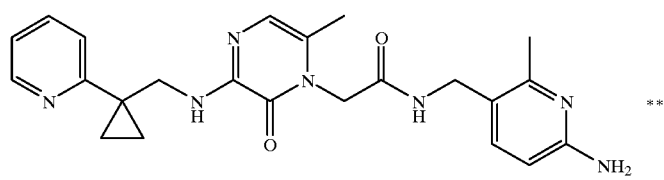 **
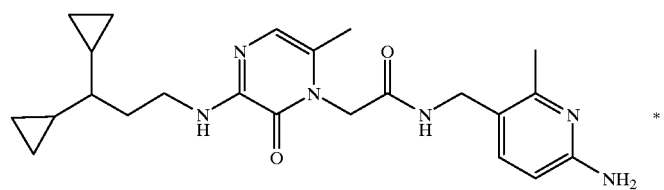 *

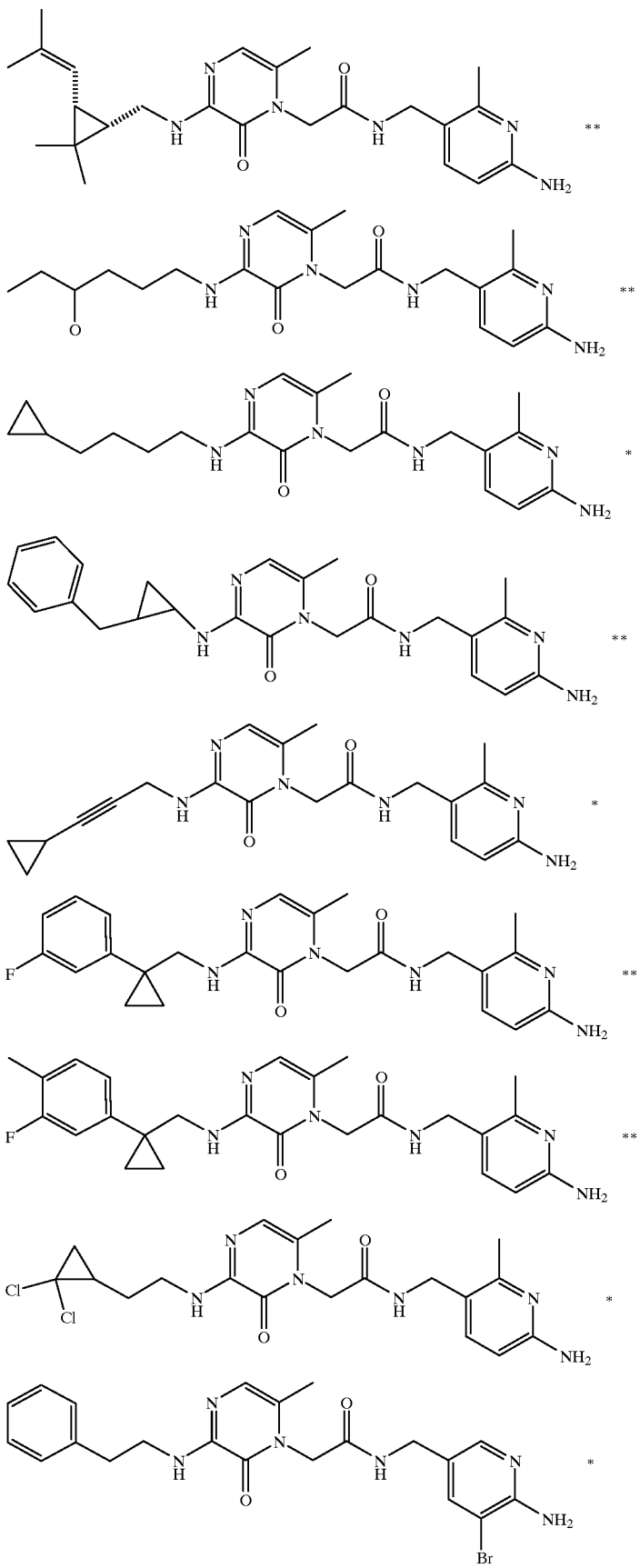

-continued
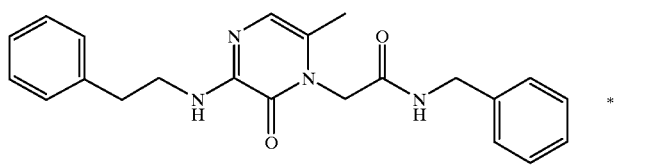 *
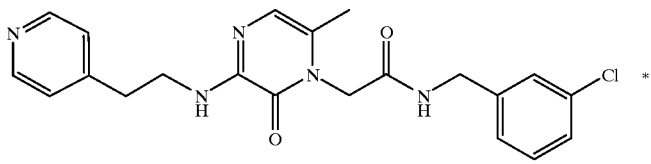 *
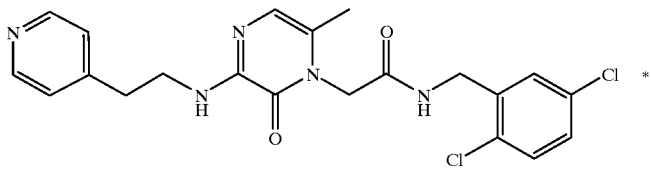 *
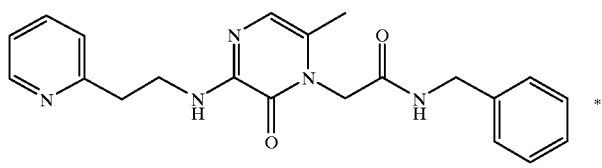 *
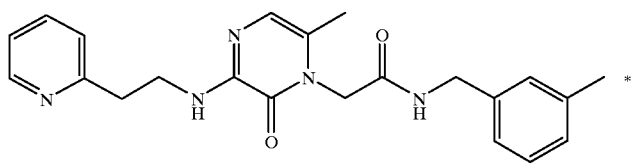 *
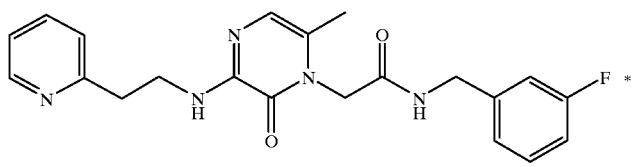 *
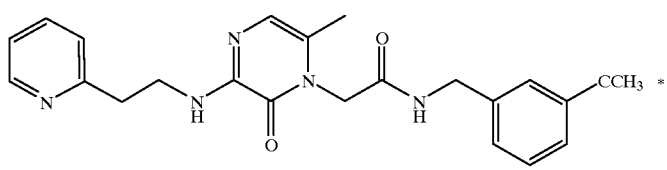 *
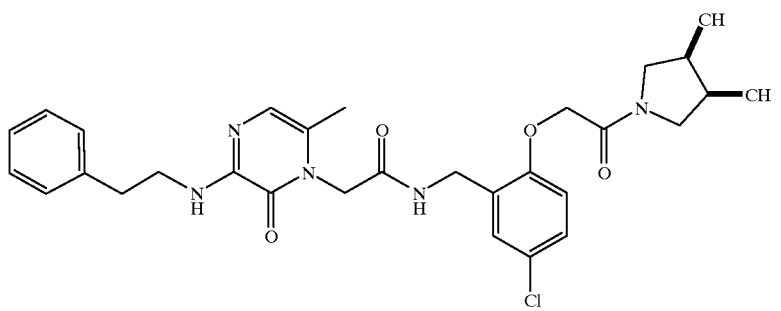 **
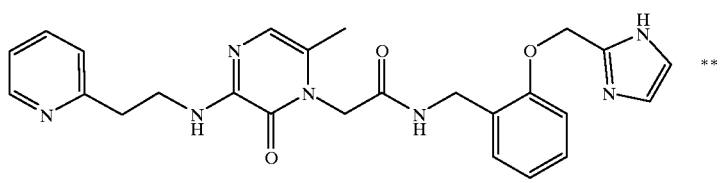 **

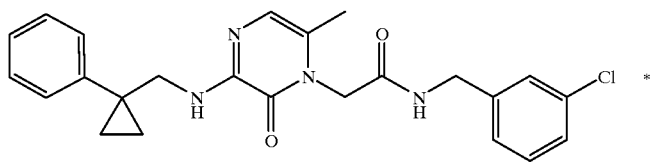
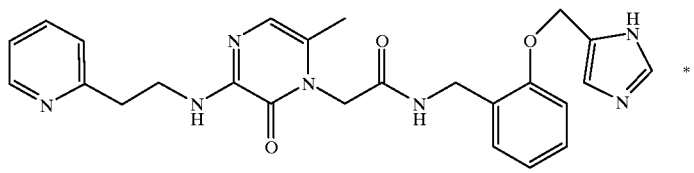
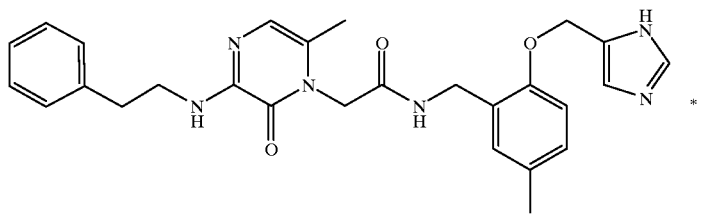
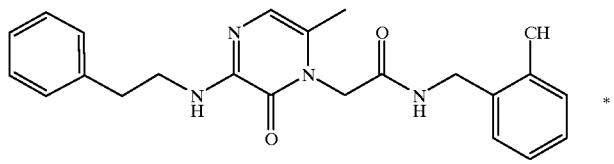
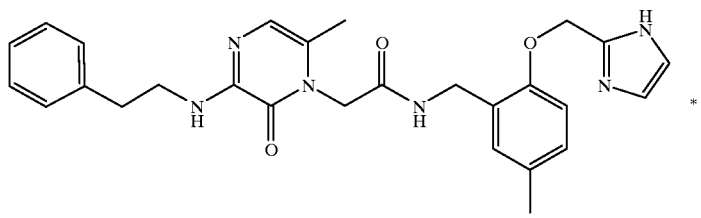
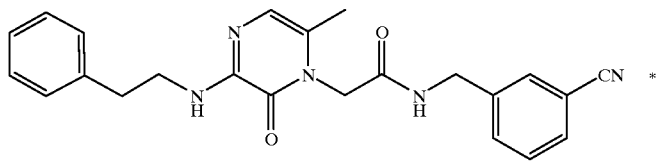
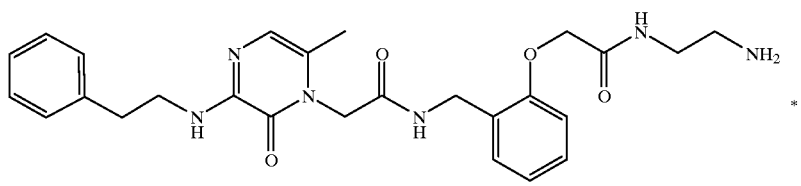
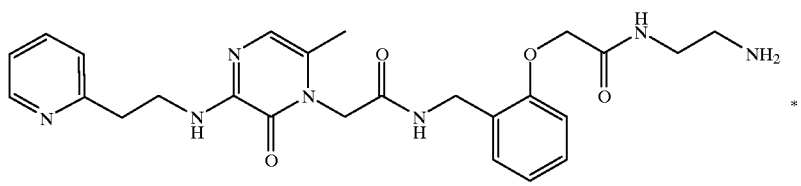

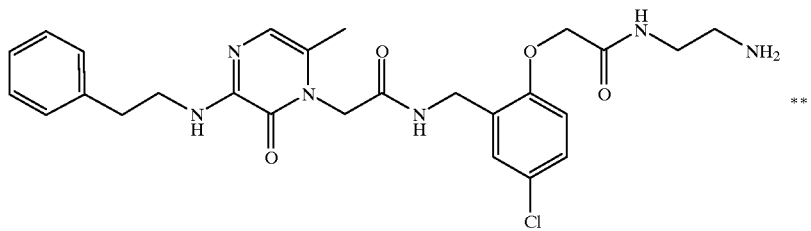
**
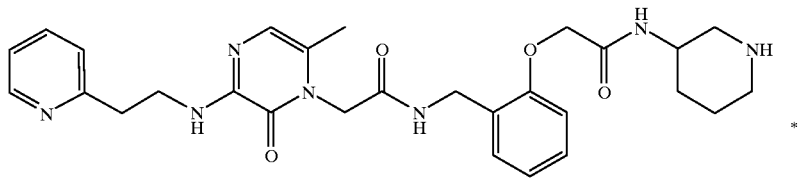
*
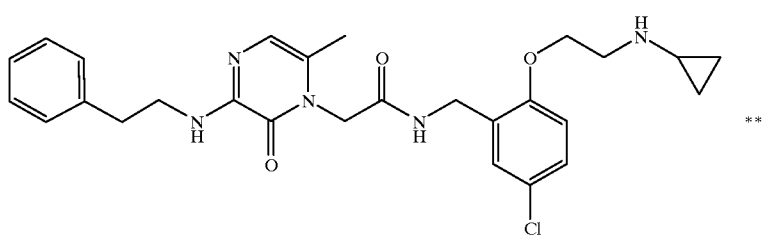
**
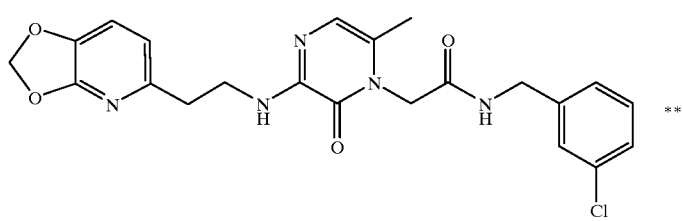
**
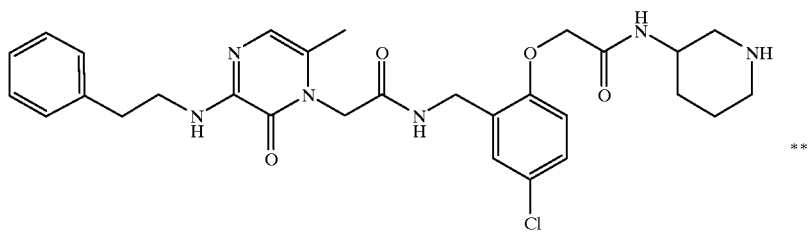
**
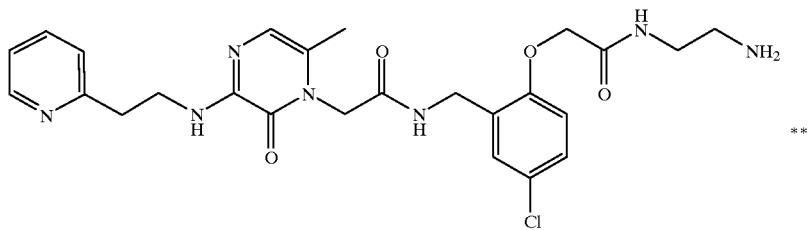
**
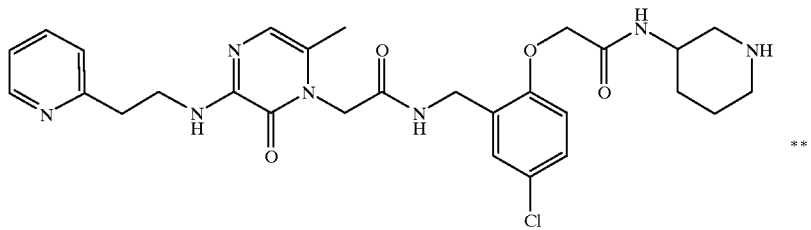
**

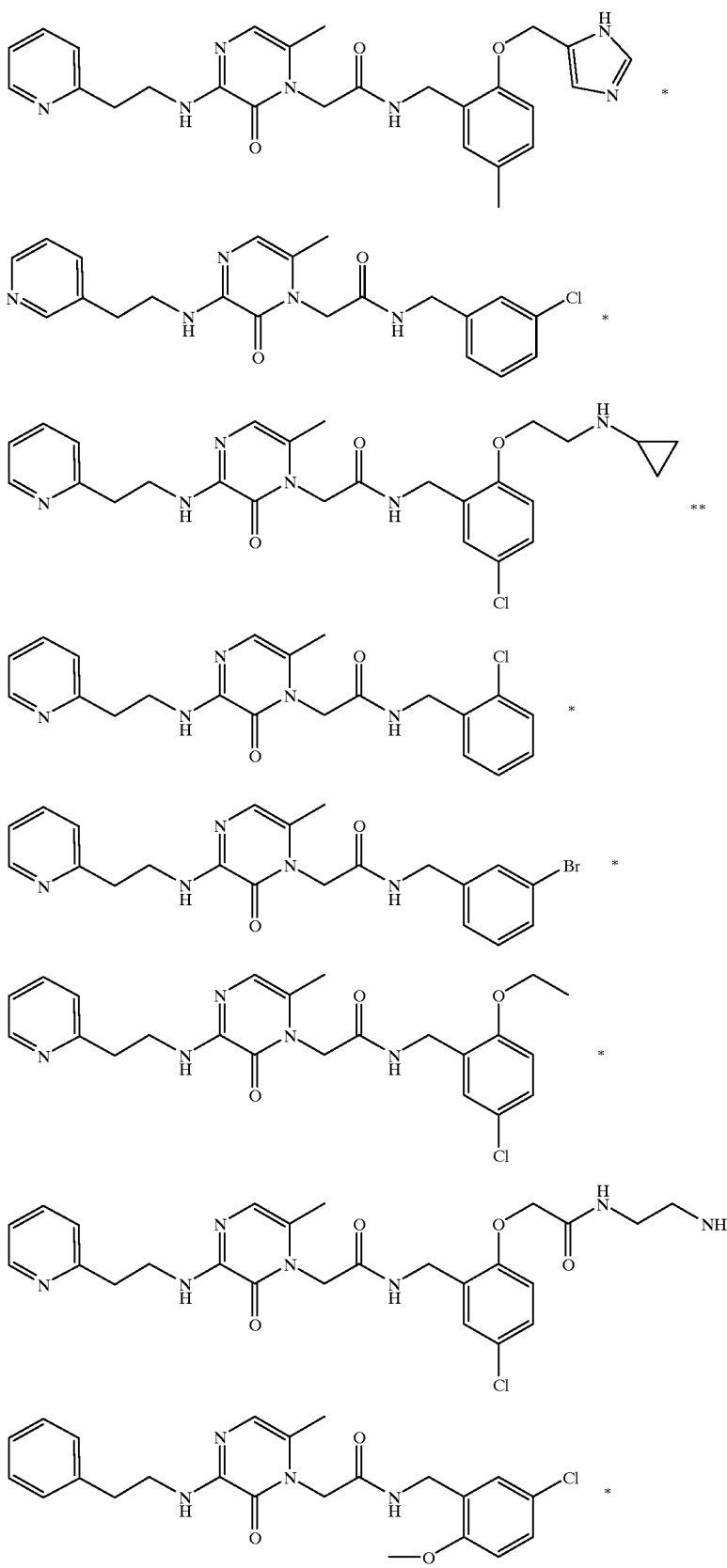

-continued

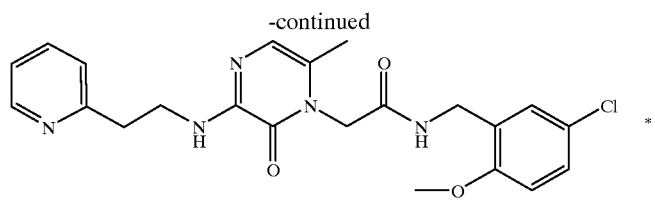

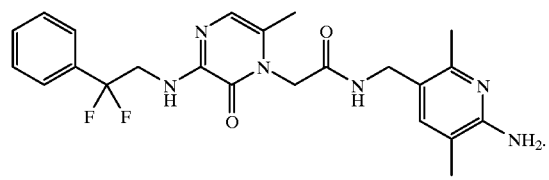

The compounds of the present invention, may have chiral centers and occur as racemates, racemic mixtures and as individual diastereomers, or enantiomers with all isomeric forms being included in the present invention. The compounds of the present invention may also have polymorphic crystalline forms, with all polymorphic crystalline forms being included in the present invention.

When any variable occurs more than one time in any constituent or in formula I, its definition on each occurrence is independent of its definition at every other occurrence. Also, combinations of substituents and/or variables are permissible only if such combinations result in stable compounds.

Some abbreviations that may appear in this application are as follows.

| ABBREVIATIONS | |
|---|---|
| Designation | Protecting Group |
| BOC (Boc) | t-butyloxycarbonyl |
| CBZ (Cbz) | benzyloxycarbonyl(carbobenzoxy) |
| TBS (TBDMS) | t-butyl-dimethylsilyl |
| Activating Group | |
| HBT(HOBT or HOBt) | 1-hydroxybenzotriazole hydrate |
| Designation | Coupling Reagent |
| BOP reagent | benzotriazol-1-yloxytris-(dimethylamino)phosphonium hexafluorophosphate |
| BOP-Cl | bis(2-oxo-3-oxazolidinyl)phosphinic chloride |
| EDC | 1-ethyl-3-(3-dimethylaminopropyl)carbodiimide hydrochloride |
| | Other |
| (BOC)$_2$O (BOC$_2$O) | di-t-butyl dicarbonate |
| n-Bu$_4$N + F— | tetrabutyl ammonium fluoride |
| nBuLi (n-Buli) | n-butyllithium |
| DMF | dimethylformamide |
| Et$_3$N (TEA) | triethylamine |
| EtOAc | ethyl acetate |
| TFA | trifluoroacetic acid |
| DMAP | dimethylaminopyridine |
| DME | dimethoxyethane |
| NMM | N-methylmorpholine |
| DPPA | diphenylphosphoryl azide |
| THF | tetrahydrofuran |
| DIPEA | diisopropylethylamine |
| | Amino Acid |
| Ile | Isoleucine |

| ABBREVIATIONS | |
|---|---|
| Phe | Phenylalanine |
| Pro | Proline |
| Ala | Alanine |
| Val | Valine |

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl); "alkoxy" represents a linear or branched alkyl group of indicated number of carbon atoms attached through an oxygen bridge; "Halo", as used herein, means fluoro, chloro, bromo and iodo; and "counterion" is used to represent a small, single negatively-charged species, such as chloride, bromide, hydroxide, acetate, trifluoroacetate, perchlorate, nitrate, benzoate, maleate, sulfate, tartrate, hemitartrate, benzene sulfonate, and the like.

The term "$C_{3-7}$cycloalkyl" is intended to include cyclopropyl, cyclobutyl, cyclopentyl, cyclohexyl and cycloheptyl, and the like.

The term "$C_{7-12}$ bicyclic alkyl" is intended to include bicyclo[2.2.1]heptyl (norbornyl), bicyclo[2.2.2]octyl, 1,1,3-trimethyl-bicyclo[2.2.1]heptyl (bornyl), and the like.

The term "aryl" as used herein except where noted, represents a stable 6- to 10-membered mono- or bicyclic ring system such as phenyl, or naphthyl. The aryl ring can be unsubstituted or substituted with one or more of $C_{1-4}$ lower alkyl; hydroxy; alkoxy; halogen; amino. The term "heteroaryl" refers to a 5- to 7- membered unsaturated ring containing 1 or 2 heteroatoms selected from O, N, or S.

The term "heterocycle" or "heterocyclic ring", as used herein except where noted, represents a stable 5- to 7-membered mono- or bicyclic or stable 9- to 10-membered bicyclic heterocyclic ring system any ring of which may be saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. Bicyclic unsaturated ring systems include bicyclic ring systems which may be partially unsaturated or fully unsaturated. Partially unsaturated bicyclic ring systems include, for example, cyclopentenopyridinyl, benzodioxan, methylenedioxyphenyl groups. Especially useful are rings containing one oxygen or sulfur, one to four nitrogen atoms, or one oxygen or sulfur combined with one or two nitrogen atoms. The heterocyclic ring may be attached at any heteroatom or carbon atom which results in the creation of a stable structure. Examples of such heterocyclic groups include piperidinyl, piperazinyl, 2-oxopiperazinyl, 2-oxopiperidinyl, 2-oxopyrrolodinyl, 2-oxoazepinyl, azepinyl, pyrrolyl, 4-piperidonyl, pyrrolidinyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isoxazolyl, isoxazolidinyl, morpholinyl, thiazolyl, thiazolidinyl, isothiazolyl, quinuclidinyl, isothiazolidinyl, indolyl, quinolinyl, isoquinolinyl, benzimidazolyl, thiadiazoyl, benzopyranyl, benzothiazolyl, benzoxazolyl, furyl, tetrahydrofuryl, tetrahydropyranyl, tetrazole, thienyl, benzothienyl, thiamorpholinyl, thiamorpholinyl sulfoxide, thiamorpholinyl sulfone, and oxadiazolyl. Morpholino is the same as morpholinyl.

The pharmaceutically-acceptable salts of the compounds of Formula I (in the form of water- or oil-soluble or dispersible products) include the conventional non-toxic salts such as those derived from inorganic acids, e.g. hydrochloric, hydrobromoic, sulfuric, sulfamic, phosphoric, nitric and the like, or the quaternary ammonium salts which are formed, e.g., from inorganic or organic acids or bases. Examples of acid addition salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methanesulfonate, 2-naphthalenesulfonate, nicotinate, nitrate, oxalate, pamoate, pectinate, persulfate, 3-phenylpropionate, picrate, pivalate, propionate, succinate, sulfate, tartrate, thiocyanate, tosylate, and undecanoate. Base salts include ammonium salts, alkali metal salts such as sodium and potassium salts, alkaline earth metal salts such as calcium and magnesium salts, salts with organic bases such as dicyclohexylamine salts, N-methyl-D-glucamine, and salts with amino acids such as arginine, lysine, and so forth. Also, the basic nitrogen-containing groups may be quaternized with such agents as lower alkyl halides, such as methyl, ethyl, propyl, and butyl chloride, bromides and iodides; dialkyl sulfates like dimethyl, diethyl, dibutyl; and diamyl sulfates, long chain halides such as decyl, lauryl, myristyl and stearyl chlorides, bromides and iodides, aralkyl halides like benzyl and phenethyl bromides and others.

Thrombin Inhibitors—Therapeutic Uses—Method of Using

Anticoagulant therapy is indicated for the treatment and prevention of a variety of thrombotic conditions, particularly coronary artery and cerebrovascular disease. Those experienced in this field are readily aware of the circumstances requiring anticoagulant therapy. The term "patient" used herein is taken to mean mammals such as primates, including humans, sheep, horses, cattle, pigs, dogs, cats, rats, and mice.

Thrombin inhibition is useful not only in the anticoagulant therapy of individuals having thrombotic conditions, but is useful whenever inhibition of blood coagulation is required such as to prevent coagulation of stored whole blood and to prevent coagulation in other biological samples for testing or storage. Thus, the thrombin inhibitors can be added to or contacted with any medium containing or suspected of containing thrombin and in which it is desired that blood coagulation be inhibited, e.g., when contacting the mammal's blood with material selected from the group consisting of vascular grafts, stents, orthopedic prosthesis, cardiac prosthesis, and extracorporeal circulation systems.

Compounds of the invention are useful for treating or preventing venous thromboembolism (e.g. obstruction or occlusion of a vein by a detached thrombus; obstruction or occlusion of a lung artery by a detached thrombus), cardiogenic thromboembolism (e.g. obstruction or occlusion of the heart by a detached thrombus), arterial thrombosis (e.g. formation of a thrombus within an artery that may cause infarction of tissue supplied by the artery), atherosclerosis (e.g. arteriosclerosis characterized by irregularly distributed lipid deposits) in mammals, and for lowering the propensity of devices that come into contact with blood to clot blood.

Examples of venous thromboembolism which may be treated or prevented with compounds of the invention include obstruction of a vein, obstruction of a lung artery (pulmonary embolism), deep vein thrombosis, thrombosis associated with cancer and cancer chemotherapy, thrombosis inherited with thrombophilic diseases such as Protein C deficiency, Protein S deficiency, antithrombin III deficiency, and Factor V Leiden, and thrombosis resulting from acquired thrombophilic disorders such as systemic lupus erythematosus (inflammatory connective tissue disease). Also with regard to venous thromboembolism, compounds of the invention are useful for maintaining patency of indwelling catheters.

Examples of cardiogenic thromboembolism which may be treated or prevented with compounds of the invention include thromboembolic stroke (detached thrombus causing neurological affliction related to impaired cerebral blood supply), cardiogenic thromboembolism associated with atrial fibrillation (rapid, irregular twitching of upper heart chamber muscular fibrils), cardiogenic thromboembolism associated with prosthetic heart valves such as mechanical heart valves, and cardiogenic thromboembolism associated with heart disease.

Examples of arterial thrombosis include unstable angina (severe constrictive pain in chest of coronary origin), myocardial infarction (heart muscle cell death resulting from insufficient blood supply), ischemic heart disease (local anemia due to obstruction (such as by arterial narrowing) of blood supply), reocclusion during or after percutaneous transluminal coronary angioplasty, restenosis after percutaneous transluminal coronary angioplasty, occlusion of coronary artery bypass grafts, and occlusive cerebrovascular disease. Also with regard to arterial thrombosis, compounds of the invention are useful for maintaining patency in arteriovenous cannulas.

Examples of atherosclerosis include arteriosclerosis.

Examples of devices that come into contact with blood include vascular grafts, stents, orthopedic prosthesis, cardiac prosthesis, and extracorporeal circulation systems The thrombin inhibitors of the invention can be administered ina such oral forms as tablets, capsules (each of which includes sustained release or timed release formulations), pills, powders, granules, elixirs, tinctures, suspensions, syrups, and emulsions. Likewise, they may be administered in intravenous (bolus or infusion), intraperitoneal, subcutaneous, or intramuscular form, all using forms well known to those of ordinary skill in the pharmaceutical arts. An effective but non-toxic amount of the compound desired can be employed as an anti-aggregation agent. For treating ocular build up of fibrin, the compounds may be administered intraocularly or topically as well as orally or parenterally.

The thrombin inhibitors can be administered in the form of a depot injection or implant preparation which may be formulated in such a manner as to permit a sustained release of the active ingredient. The active ingredient can be compressed into pellets or small cylinders and implanted subcutaneously or intramuscularly as depot injections or implants. Implants may employ inert materials such as biodegradable polymers or synthetic silicones, for example, Silastic, silicone rubber or other polymers manufactured by the Dow-Corning Corporation.

The thrombin inhibitors can also be administered in the form of liposome delivery systems, such as small unilamellar vesicles, large unilamellar vesicles and multilamellar vesicles. Liposomes can be formed from a variety of phospholipids, such as cholesterol, stearylamine or phosphatidylcholines.

The thrombin inhibitors may also be delivered by the use of monoclonal antibodies as individual carriers to which the compound molecules are coupled. The thrombin inhibitors may also be coupled with soluble polymers as targetable drug carriers. Such polymers can include polyvinlypyrrolidone, pyran copolymer, polyhydroxypropyl-methacrylamide-phenol, polyhydroxyethyl-aspartamide-phenol, or polyethyleneoxide-polylysine substituted with palmitoyl residues. Furthermore, the thrombin inhibitors may be coupled to a class of biodegradable polymers useful in achieving controlled release of a drug, for example, polylactic acid, polyglycolic acid, copolymers of polylactic and polyglycolic acid, polyepsilon caprolactone, polyhydroxy butyric acid, polyorthoesters, polyacetals, polydihydropyrans, polycyanoacrylates and cross linked or amphipathic block copolymers of hydrogels.

The dosage regimen utilizing the thrombin inhibitors is selected in accordance with a variety of factors including type, species, age, weight, sex and medical condition of the patient; the severity of the condition to be treated; the route of administration; the renal and hepatic function of the patient; and the particular compound or salt thereof employed. An ordinarily skilled physician or veterinarian can readily determine and prescribe the effective amount of the drug required to prevent, counter, or arrest the progress of the condition.

Oral dosages of the thrombin inhibitors, when used for the indicated effects, will range between about 0.01 mg per kg of body weight per day (mg/kg/day) to about 30 mg/kg/day, preferably 0.025–7.5 mg/kg/day, more preferably 0.1–2.5 mg/kg/day, and most preferably 0.1–0.5 mg/kg/day (unless specificed otherwise, amounts of active ingredients are on free base basis). For example, an 80 kg patient would receive between about 0.8 mg/day and 2.4 g/day, preferably 2–600 mg/day, more preferably 8–200 mg/day, and most preferably 8–40 mg/kg/day. A suitably prepared medicament for once a day administration would thus contain between 0.8 mg and 2.4 g, preferably between 2 mg and 600 mg, more preferably between 8 mg and 200 mg, and most preferably 8 mg and 40 mg, e.g., 8 mg, 10 mg, 20 mg and 40 mg. Advantageously, the thrombin inhibitors may be administered in divided doses of two, three, or four times daily. For administration twice a day, a suitably prepared medicament would contain between 0.4 mg and 4 g, preferably between 1 mg and 300 mg, more preferably between 4 mg and 100 mg, and most preferably 4 mg and 20 mg, e.g., 4 mg, 5 mg, 10 mg and 20 mg.

Intravenously, the patient would receive the active ingredient in quantities sufficient to deliver between 0.025–7.5 mg/kg/day, preferably 0.1–2.5 mg/kg/day, and more preferably 0.1–0.5 mg/kg/day. Such quantities may be administered in a number of suitable ways, e.g. large volumes of low concentrations of active ingredient during one extended period of time or several times a day, low volumes of high concentrations of active ingredient during a short period of time, e.g. once a day. Typically, a conventional intravenous formulation may be prepared which contains a concentration of active ingredient of between about 0.01–1.0 mg/ml, e.g. 0.1 mg/ml, 0.3 mg/ml, and 0.6 mg/ml, and administered in amounts per day of between 0.01 ml/kg patient weight and 10.0 ml/kg patient weight, e.g. 0.1 ml/kg, 0.2 ml/kg, 0.5 ml/kg. In one example, an 80 kg patient, receiving 8 ml twice a day of an intravenous formulation having a concentration of active ingredient of 0.5 mg/ml, receives 8 mg of active ingredient per day. Glucuronic acid, L-lactic acid, acetic acid, citric acid or any pharmaceutically acceptable acid/conjugate base with reasonable buffering capacity in the pH range acceptable for intravenous administration may be used as buffers. Consideration should be given to the solubility of the drug in choosing an The choice of appropriate buffer and pH of a formulation, depending on solubility of the drug to be administered, is readily made by a person having ordinary skill in the art.

The compounds can also be administered in intranasal form via topical use of suitable intranasal vehicles, or via transdermal routes, using those forms of transdermal skin patches well known to those of ordinary skill in that art. To be administered in the form of a transdermal delivery system, the dosage administration will, or course, be continuous rather than intermittent throughout the dosage regime.

The thrombin inhibitors are typically administered as active ingredients in admixture with suitable pharmaceutical diluents, excipients or carriers (collectively referred to herein as "carrier" materials) suitably selected with respect to the intended form of administration, that is, oral tablets, capsules, elixers, syrups and the like, and consistent with convention pharmaceutical practices.

For instance, for oral administration in the form of a tablet or capsule, the active drug component can be combined with an oral, non-toxic, pharmaceutically acceptable, inert carrier such as lactose, starch, sucrose, glucose, methyl cellulose, magnesium stearate, dicalcium phosphate, calcium sulfate, mannitol, sorbitol and the like; for oral administration in liquid form, the oral drug components can be combined with any oral, non-toxic, pharmaceutically acceptable inert carrier such as ethanol, glycerol, water and the like. Moreover, when desired or necessary, suitable binders, lubricants, distintegrating agents and coloring agents can also be incorporated into the mixture. Suitable binders include starch, gelatin, natural sugars such as glucose or beta-lactose, corn-sweeteners, natural and synthetic gums such as acacia, tragacanth or sodium alginate, carboxymethylcellulose, polyethylene glycol, waxes and the like. Lubricants used in these dosage forms include sodium oleate, sodium stearate, magnesium stearate, sodium benzoate, sodium acetate, sodium chloride and the like. Disintegrators include, without limitation, starch methyl cellulose, agar, bentonite, xanthan gum and the like.

Typical tablet cores suitable for administration of thrombin inhibitors are comprised of, but not limited to, the following amounts of standard ingredients:

| Excipient | Suggested Ranges of Composition for Excipients in Uncoated Tablet Cores | | |
|---|---|---|---|
| | General Range (%) | Preferred Range (%) | Most Preferred Range (%) |
| mannitol | 10–90 | 25–75 | 30–60 |
| microcrystalline cellulose | 10–90 | 25–75 | 30–60 |
| magnesium stearate | 0.1–5.0 | 0.1–2.5 | 0.5–1.5 |

Mannitol, microcrystalline cellulose and magnesium stearate may be substituted with alternative pharmaceutically acceptable excipients.

The thrombin inhibitors can also be co-administered with suitable anti-platelet agents, including, but not limited to, fibrinogen receptor antagonists (e.g. to treat or prevent unstable angina or to prevent reocclusion after angioplasty and restenosis), anticoagulants such as aspirin, thrombolytic agents such as plasminogen activators or streptokinase to achieve synergistic effects in the treatment of various vascular pathologies, or lipid lowering agents including antihypercholesterolemics (e.g. HMG CoA reductase inhibitors such as lovastatin, HMG CoA synthase inhibitors, etc.) to treat or prevent atherosclerosis. For example, patients suffering from coronary artery disease, and patients subjected to angioplasty procedures, would benefit from coadministration of fibrinogen receptor antagonists and thrombin inhibitors. Also, thrombin inhibitors enhance the efficiency of tissue plasminogen activator-mediated thrombolytic reperfusion. Thrombin inhibitors may be administered first following thrombus formation, and tissue plasminogen activator or other plasminogen activator is administered thereafter.

Typical doses of thrombin inhibitors of the invention in combination with other suitable anti-platelet agents, anticoagulation agents, or thrombolytic agents may be the same as those doses of thrombin inhibitors administered without coadministration of additional anti-platelet agents, anticoagulation agents, or thrombolytic agents, or may be substantially less that those doses of thrombin inhibitors administered without coadministration of additional anti-platelet agents, anticoagulation agents, or thrombolytic agents, depending on a patient's therapeutic needs.

The following synthetic methods can be used to prepare the compounds of the present invention:

EXAMPLE 1

Preparation of 3-(2-Phenethylaniino)-6-methyl-1-(2-amino-3,6-dimethyl-5-methylcarboxamidomethyllvridinyl)-dyrazinone dihydrochloride (1-4)

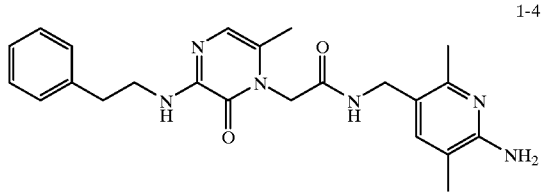

1-4

Step A: 2-amino-5-bromo-3,6-dimethylpyridine (1-1) Bromine (1.48 mL, 28.8 mmol) was added dropwise to a stirred solution of 2-amino-3,6-dimethylpyridine (3.52 g, 28.8 mmol, which was prepared from 2,5-lutidine according to the procedure of Albert and Willette: *J. Chem. Soc.*, 1964, 4063) in glacial acetic acid (30 mL) at 10° C. After 15 min the thick precipitate was collected by filtration, washing with acetic acid and ether. The resulting white crystalline solid was partitioned between ethyl acetate and brine which was basified by adding saturated sodium carbonate solution. The organic layer was dried ($Na_2SO_4$) and evaporated in vacuo to give 1-1 as a white solid: $^1$H NMR ($CDCl_3$)δ 5 2.08 (s, 3 H), 2.45 (s, 3 H), 4.33 (br s, 2 H), 7.36 (s, 1 H).

Step B: 2-amino-5-cyano-3,6-dimethylpyridine (1-2)

A mixture of 1-1 (3.07 g, 15.3 mmol) and copper (I) cyanide (1.64 g, 18.4 mol) in DMF (4 mL) was heated to reflux for 4 h. The DMF was evaporated in vacuo and the residue was crushed to a fine powder which was partitioned between ethyl acetate and 10% sodium cyanide solution. The organic layer which contained a large amount of a suspension was dried ($Na_2SO_4$), filtered through a bed of celite, washing the drying agent and filter cake with THF to dissolve the organic solids, and evaporated in vacuo to a tan solid. The crude product was heated to reflux as a suspension in ethyl acetate (20 mL), then was cooled and the solids collected by filtration, and dried to give 1-2 as a tan solid: $^1$H NMR ($CDCl_3$)δ 2.10 (s, 3 H), 2.54 (s, 3 H), 4.86 (br s, 2 H), 7.39 (s, 1 H).

Step C: 2-amino-5-aminomethyl-3,6-dimethylpyridine dihydrochloride (give 1-3)

A mixture of give 1-2 (1.47 g, 10 mmol) and 10% Pd/C (1.0 g) in ethanol (20 mL), methanol (16 mL), concentrated HCl (2 mL, 24 mmol)) and water (2 mL) was shaken on a Parr apparatus at 60 psi for 16 h. The reaction was filtered through celite, rinsing with ethanol and was evaporated in vacuo, azeotroping with ethanol, to give a solid. The crude product was heated to relux as a suspension in ethanol (20 mL), then was cooled and the solids collected by filtration, washing with ethanol and ether, and dried to give 1-3 as a white crystalline solid: $^1$H NMR ($D_6$ DMSO):δ 2.14 (s, 3 H), 2.52 (s, 3 H), 3.91 (br d, 2 H), 7.83 (br s, 1 H), 7.86 (s, 1 H), 8.38 (br s, 2 H).

Step D: 3-(2-Phenethylamino)-6-methyl-1-(2-amino-3,6-dimethyl-5-methylcarboxamidomethylpyridinyl)-pyrazinone dihydrochloride (1-4)

EDC•HCl (125 mg, 0.65 mmol) was added at 0° C. to a stirred mixture of 3-(2-phenethylamino)-6-methyl-1-carboxymethyl-pyrazinone (144 mg, 0.5 mmol), give 1-3 (112 mg, 0.5 mmol), HOBT•$H_2O$ (88 mg, 0.65 mmol) and N-methylmorpholine (0.236 mL, 2.15 mmol) in dry DMF (2 mL). After 3 h at R.T. the thick mixture was poured into water (40 mL) and the precipitate was collected by filtration, washing with water, ethanol and ether to give the free base of the title compound as a cake. This was crushed to a fine powder, suspended in ethanol (10 mL) and ethanolic HCl (9.9M, 0.15 mL) was added. The resulting solution was evaporated in vacuo to a solid which was heated to reflux in ethanol (10 mL), cooled, filtered, washing the solids with ethanol and ether, and dried to give 1–14 as a white crystalline solid, m.p. >230° C.;

$^1$H NMR (DMSO-$d_6$):δ 2.10 (s, 3H, $CH_3$), 2.14 (s, 3H, $CH_3$), 2.43 (s, 3H, $CH_3$), 2.91 (t, J=7.5 Hz, 2H, $PhCH_2$), 3.63 (br q, 2H, $CH_2NH$), 4.16 (d, J=5.4 Hz, 2H, $CONHCH_2$), 4.63 (s, 2H, $CH_2CO$), 6.69 (s, 1H, pyrazinone H-5), 7.21–7.33 (m, 5H, Ph), 7.63 (br s, 2H, $NH_2$), 7.66 (s, 1H, pyridine H-4), 8.77 (br t, J=5.4 Hz, 1H, CONH).

EXAMPLE 2

Preparation of 3-(2-Phenethylamino)-6-methyl-1-(2-amino-3,4-dimethyl-5-methylcarboxamidomethylpyridinyl)-pyrazinone dihydrochloride (2-1)

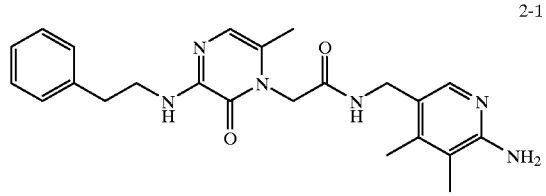

2-1

2-1 was prepared using the procedures of Example 1, Steps A–D starting from 3,4-lutidine, to give 2-1 as a white crystalline solid m.p. >230° C.; $^1$H NMR (DMSO-$d_6$): δ 2.11 (s, 3H, $CH_3$), 2.12 (s, 3H, $CH_3$), 2.27 (s, 3H, $CH_3$), 2.91 (t, J=7.5 Hz, 2H, PhCH$_2$), 3.63 (br q, 2H, CH$_2$NH), 4.24 (d, J=5.4 Hz, 2H, CONHCH$_2$), 4.64 (s, 2H, CH$_2$CO), 6.68 (s, 1H, pyrazinone H-5), 7.20–7.33 (m, 5H, Ph), 7.73 (br s, 3H, NH$_2$, pyridine H-6), 8.71 (br t, J=5.4 Hz, 1H, CONH).

EXAMPLE 3

Preparation of 3-[2-(3-Fluorophenethylamnino)]-6-methyl-1-(2-amino-3,6-dimethyl-5-methylcarboxamidomethylpyridinyl)-pyrazinone dihydrochloride (3-1)

3-1

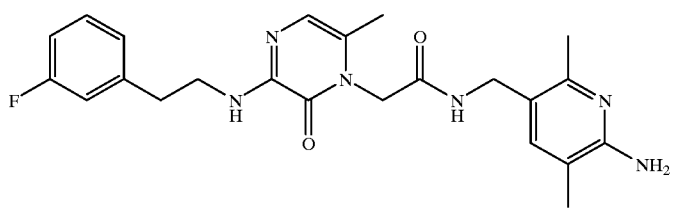

EDC•HCl (63 mg, 0.33 mmol) was added at 0° C. to a stirred mixture of 3-[2-(3-fluorophenethylamino)]-6-methyl-1-carboxymethyl pyrazinone (84 mg, 0.275 mmol), give 1-3 (62 mg, 0.275 mimol), HOBT•H$_2$O (45 mg, 0.33 mmol) and N-methylmorpholine (0.152 mL, 1.375 mmol) in dry DMF (2.4 mL). After 16 h at R.T. the volatiles were evaporated in vacuo and the residue was suspended in dilute sodium carbonate solution and collected by filtration, washing with water, and dried to give the free base of the title compound. This was suspended in ethanol (4.5 mL) and ethanolic HCl (9.9M, 0.2 mL) was added. After stirring for 1.5 h, the precipitate was collected by filtration, washing with ethyl acetate, and the solids were resuspended in refluxing ethyl acetate, which was then cooled filtered and the solids dried give 3-1 as a white crystalline solid, m.p. >220° C.; $^1$H NMR (CD$_3$OD): δ 2.19 (d, J=1.1 Hz, 3H, pyrazinone CH$_3$), 2.22 (s, 3H, CH$_3$), 2.50 (s, 3H, CH$_3$), 3.01 (t, J=7.4 Hz, 2H, PhCH$_2$), 3.68 (t, J=7.4 Hz, 2H, CH$_2$NH), 4.32 (d, J=5.7 Hz, 2H, CONHCH$_2$), 4.76 (s, 2H, CH$_2$CO), 6.59 (d, J=1.1 Hz, 1H, pyrazinone H-5), 6.97–7.35 (m, 4H, C$_6$H$_4$F), 7.73 (s, 1H, pyridine H-4), 8.84 (br t, 1H, CONH).

EXAMPLE 4

Preparation of 2-Cyclobutylethylamine hydrochloride (4-1)

4-1

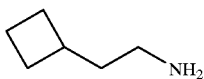

A mixture of sodium cyanide (0.74 g, 15.1 mmol) and bromomethylcyclobutane (1.7 mL, 15.1 mmol) in dry DMF (37.5 mL) was stirred at 100° C. for 16 h. The resulting mixture was cooled and partitioned between water and methylene chloride. The organic layer was dried (Na2SO4) and the volatiles removed by distillation to leave a mixture of cyclobutylacetonitrile and DMF. This residue was partitioned between water (500 mL) and hexanes (50 mL). The organic layer was washed twice with water (100 mL), dried (Na2SO4) and the hexanes removed by distillation to give cyclobutylacetonitrile as an oil. This was dissolved in 1:1 ethanol/1 N HCl (200 mL), 10% Pd/C (546 mg) was added and the mixture was stirred under an atmosphere of hydrogen. After 16 h, the mixture was filtered through celite, and evaporated in vacuo to give 4-1 as an orange solid; $^1$H NMR (DMSO d$_6$): δ 1.57–1.70 (m, 4H), 1.79–1.84 (m, 2H), 2.03 (m, 2H), 2.30 (m, 1H), 2.63 (br s, 2H), 8.09 (br s, 2H).

EXAMPLE 5

Preparation of 3-(2-Cyclobutylethylamino)-6-methyl-i-(2-amino-6-methyl-5-methylcarboxamidomethylpyridinyl)-pyrazinone dihydrochloride (5-6)

5-6

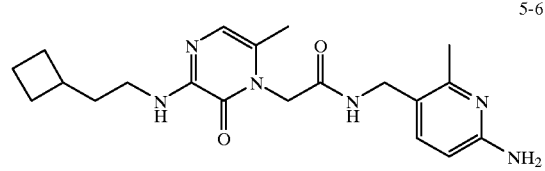

Step A: Benzyl-N-(1-cyanoethyl)glvcine hydrochloride (5-1)

TMSCN (18.8 mL, 141 mmol) was added cautiously (the reaction is exothermic) to a stirred solution of benzylglycine free base (23.3 g, 141 mmol—from the HCl salt by partition between EtOAc and brine basified with saturated Na$_2$CO$_3$ solution) and acetaldehyde (7.88 mL, 141 mmol) in methylene chloride (50 mL). After 4 h the volatiles were removed in vacuo and the residue was taken up in EtOAc and was washed with brine, dried (Na$_2$SO$_4$) and evaporated in vacuo to an oil. The oil was redissolved in EtOAc and 9.9 M HCl in EtOH (15.25 mL, 151 mmol) was added to give a crystalline precipitate which was isolated by filtration, washing with EtOAc and Et$_2$O to give 5-1: $^1$H NMR (CD$_3$OD): δ 1.70 (d, J=7.0 Hz, 3H, CH$_3$), 4.16 (d, J=16.8 Hz, 1H, CH$_A$H$_B$), 4.21 (d, J=16.8 Hz, 1H, CH$_A$H$_B$), 4.64 (q, J=7.0 Hz, a-CH), 5.31 (s, 2H, CH$_2$O), 7.35–7.44 (m, 5H, Ph).

Step B: 1-Benzyloxycarbonylmethyl-3, 5-dichloro-6-methylpyrazinone (5-2)

A stirred mixture of oxalyl chloride (40.4 mL, 463 mmol) and 5-1 (29.51 g, 116 mmol) in 1,2-dichlorobenzene 110 mL) was heated to 100° C. for 15 h. The volatiles were evaporated in vacuo and the residue was purified by flash column chromatography on silica (eluting with hexanes followed by 30% ethyl acetate/hexanes) to give a solid which was heated to reflux in 2:5 EtOAc/hexanes (140 mL), cooled, and collected by filtration to give 5-2 as a pale green crystalline solid: $^1$H NMR (CDCl$_3$): δ 2.35 (s, 3H, CH$_3$), 4.88 (s, 2H, CH$_2$), 5.24 (s, 2H, CH$_2$), 7.38 (m, 5H, Ph).

Step C: 3-(2-Cyclobutylethylamino)-5-chloro-6-methyl-1-(benzyloxycarbonylmethyl)-dyrazinone (5-3)

2-Cyclobutylethylamine hydrochloride (95 mg, 0.7 mmol) was added to a stirred mixture of 5-2 (208 mg, 0.636 mmol) and sodium hydrogen carbonate (112 mg, 1.34 mmol) in water (0.66 mL) and toluene (1.27 mL) and the resulting two phase mixture was heated to 80° C. After 4 h the reaction was cooled and partitioned between methylene chloride and 10% citric acid solution. The organic layer was dried (Na$_2$SO$_4$) and evaporated in vacuo to give 5-3 as a crystalline solid.

Step D: 3-(2-Cyclobutylethylamino)-5-chloro-6-methyl-1-carboxymethylpyrazinone (5-4)

LiOH•H$_2$O (40 mg, 0.954 mmol) was added to a stirred suspension of the product from Step C in 4:4:1 THF/MeOH/H$_2$O (7.2 mL). After 16 h the solution was diluted with water and was washed with EtOAc. The aqueous layer was acidified with 15% KHSO$_4$ solution and was extracted twice with methylene chloride. The methylene chloride layers were combined, dried (Na$_2$SO$_4$) and evaporated in vacuo. The crude product was purified by flash column chromatography on silica (2% acetic acid/chloroform/methanol gradient, 2–5% methanol) to give 5-4 as a white solid: $^1$H NMR (CD$_3$OD): δ 1.66–1.81 (m, 4H), 1.82–1.93 (m, 2H), 2.05–2.13 (m, 2H), 2.27 (s, 3H, Me), 2.33–2.39 (m, 1H), 3.28 (obscured t, J=6.4 Hz, 2H, CH$_2$NH), 4.79 (s, 2H, CH$_2$CO$_2$).

Step E: 3-(2-Cyclobutylethylamino)-6-methyl-1-carboxymethylpyrazinone (5-5)

5-4 (43.5 mg, 0.145 mmol) was added to a stirred solution of potassium hydroxide (85% by weight, 25.4 mg, 0.384 mmol) in water (2.1 mL). After degassing the resulting solution with nitrogen, 10% Pd/C (22 mg) was added and the mixture was stirred under a hydrogen filled balloon. After 4.5 h, the mixture was filtered through celite, washing the cake with water. The filtrate was acidified with 3N KHSO$_4$ and evaporated in vacuo. The solids were extracted with 10% methanol/chloroform (30 mL), removing the undissolved inorganic solids by filtration and the filtrate was evaporated in vacuo to give 5-5 as a glass: $^1$H NMR (CD$_3$OD): selected signals δ 2.21 (d, J=1.1 Hz, 3H, CH$_3$), 6.59 (q, J=1.1 Hz, 1H, pyrazinone-5).

Step F: 3-(2-Cyclobutylethylaniino)-6-methyl-1-(2-amino-6-methyl-5-methylcarboxamidomethylpyridinyl)-pyrazinone dihydrochloride (5-6)

EDC•HCl (33.4 mg, 0.174 mmol) was added to a stirred mixture of 5-5 (38.6 mg, 0.145 mmol), 2-amino-5-aminomethyl-6-methylpyridine dihydrochloride (25.2 mg, 0.145 mmol), HOBT.H$_2$O (23.5 mg, 0.174 mmol) and N-methylmorpholine (0.080 mL, 0.725 mmol) in dry DMF (1.25 mL). After 5 h, the mixture ws diluted with water (2 mL) and saturated sodium carbonate solution (2.5 mL) was added to give a precipitate which was collected by filtration, washing with water to give the title compound as the free base. This was suspended in ethanol (2 mL) and ethanolic HCl (9.9M, 0.04 mL) was added with stirring. The solution was evaporated in vacuo to give 5-6 as a crystalline solid, m.p. >200° C.; $^1$H NMR (Free base, DMSO-d$_6$): δ 1.61 (m, 4H), 1.78 (m, 2H), 2.03 (m, 2H), 2.03 (s, 3H, CH$_3$), 2.23 (s, 3H, CH$_3$), 2.27 (m, 1H), 3.14 (q, J=6.1 Hz, 2H, CH$_2$NH), 4.10 (d, J=5.1 Hz, 2H, CONHCH$_2$), 4.57 (s, 2H, CH$_2$CO), 5.74 (s, 2H, NH$_2$), 6.22 (d, J=7.8 Hz, 1H, pyridine H-3), 6.59 (s, 1H, pyrazinone H-5), 6.73 (br t, 1H, NH), 7.19 (d, J=7.8 Hz, 1H, pyridine H-4), 8.43 (br t, 1H, NH).

EXAMPLE 6

Preparation of 3-(2-Phenethylamino)-6-methyl-1-(2-amino-3-methyl-5-methylcarboxamidomethylpyridinyl)-pyrazinone (6-1)

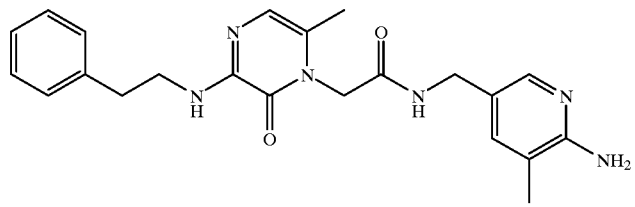

6-1

EDC•HCl (115 mg, 0.60 mmol) was added to a stirred mixture of 3-(2-phenethylamino)-6-methyl-1-carboxymethylpyrazinone (144 mg, 0.50 mmol), 2-amino-5-aminomethyl-3-methylpyridine dihydrochloride (105 mg, 0.50 mmol), HOBT•H$_2$O (81 mg, 0.60 mmol) and N-methylmorpholine (0.275 mL, 2.5 mmol) in dry DMF (4.3 mL). After 4 h the volatiles were evaporated in vacuo and the residue was suspended in dilute sodium carbonate solution and collected by filtration, washing with water, and dried to give the crude free base of the title compound. This material was purified by flash column chromatography on silica (methanol/chloroform gradient, 5-10% methanol) to give 6-1 as a white crystalline solid, m.p. >200° C.; $^1$H NMR (DMSO-d$_6$): δ 2.02 (s, 3H, CH$_3$), 2.04 (s, 3H, CH$_3$), 2.85 (t, J=7.4 Hz, 2H, PhCH$_2$), 3.48 (q, J=6.9 Hz, 2H, CH$_2$NH), 4.09 (d, J=5.5 Hz, 2H, CONHCH$_2$), 4.58 (s, 2H, CH$_2$CO), 5.60 (s, 2H, NH2), 6.64 (s, 1H, pyrazinone H-5), 6.80 (br t, J=5.6 Hz, 1H, NH), 7.13 (s, 1H, pyridine H-4), 7.17–7.31 (m, 5H, Ph), 7.69 (s, 1H, pyridine H-6), 8.51 (br t, J=5.6 Hz, 1H, CONH).

EXAMPLE 7

Preparation of 3-(2,2-difluoro-2-phenylethylamino)-1-(2-amino-6-methyl-5-methylenecarboxamidomethylpyridinyl)-6-methyl-pyrazin(1H)-2-one bis-TFA salt (7-8)

7-8

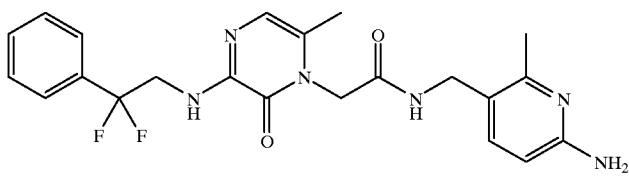

Step A: N-(Ethoxycarbonylmethyl)-N'-(2-hydroxy-1-propyl) oxamide (7-1)

To a stirred solution of 6.13 g (30.2 mmol) of ethyl N-(ethyl oxalyl)glycinate (prepared according to Krapcho et al J. Het. Chem., 1995, 32, 1693) in 30 mL of abs. ethanol, was added 2.33 mL (30.2 mmol) of 1-amino-2-propanol in one portion. The reaction solidified over a period of stirring under Ar for 2 h. The residue was dissolved in 50 mL of CHCl₃, rotovaped to dryness and reconcentrated from 100 mL of CHCl₃ and dried under reduced pressure at rt to give 7-1 as a colorless solid: $^1$H NMR (CDCl₃) δ 7.88 (br s, 1H), 7.77 (br s, 1H), 4.24 (q, 2H, 7.1 Hz), 4.09 (d, 2H, 5.9 Hz), 3.98 (br s, 1H), 3.55-3.45 (m, 1H), 3.25-3.17 (m, 1H), 2.13 (br s, 1H), 1.30 (t, 3H, 7.1 Hz), 1.23 (d, 3H, 6.3 Hz).

Step B: N-(Ethoxycarbonylmethyl)-N'-(2-oxo-1-propyl) oxamide (7-2)

To a stirred slurry of 3.98 g (17.1 mmol) of 7-1 in 24 mL of H₂O under Ar at 50° C. was added 36 mg (0.17 mmol) of ruthenium (III) chloride hydrate. The flask was removed from the heating bath, and a solution of 2.59 g (17.1 mmol) of sodium bromate in 24 mL of H₂O was added dropwise so that the temperature of the reaction stayed below 60° C. The reaction was allowed to come to rt, and then diluted with EtOAc and brine. The aqueous layer was extracted with two portions of EtOAc, and then saturated with solid NaCl and extracted again. The combined organic layers were washed with brine, dried over Na₂SO₄ and treated with activated carbon. Evaporation of the solvents and drying at reduced pressure gave 7-2 as a colorless solid: $^1$H NMR (CDCl₃) δ 7.88 (br s, 1H), 7.80 (br s, 1H), 4.24 (q, 2H, 7.1 Hz), 4.20 (d, 2H, 5.1 Hz), 4.09 (d, 2H, 5.7 Hz), 2.23 (s, 3H), 1.35-1.25 (m, 3H).

Step C: 1-(Ethoxycarbonylmethyl)-3-hydroxy-6-methyl-pyrazinone (7-3)

A solution of 3.43 g (14.9 mmol) of 7-2, 1.15 mL (14.9 mmol) of TFA and 2.104 mL (14.9 mmol) of trifluoroacetic anhydride in 60 mL of acetic acid was heated to 80° C. under a slow stream of Ar for 7 h. After HPLC analysis of the reaction progress, an additional 766 μL (9.9 mmol) of TFA and 1.4 mL (9.9 mmol) of trifluoroacetic anhydride were added and the reaction mixture was heated for an additional 24 h. After standing at rt for several hours, the solvents were removed at reduced pressure, and the residue digested in 7 mL of acetic acid at 60° C. for 10 min, then 35 mL of isopropyl acetate (iPAc) was added dropwise to the warm mixture. After the addition, the slurry was allowed to cool to rt, filtered, and washed with 1:5 HOAc-iPAc. The solid was air dried to give 7-3 as an almost colorless solid: $^1$H NMR (CDCl₃) δ 10.92 (br s, 1H), 6.185 (s, 1H), 4.66 (s, 2H), 4.25 (q, 2H, 7.1 Hz), 2.08 (s, 3H), 1.30 (t, 3H, 7.1 H Step D: 3-Bromo-1-(ethoxycarbonylmethyl)-6-methylpyrazinone (7-4)

A stirred slurry of 505 mg (2.38 mmol) of 7-3 and 756 mg (2.64 mmol) of phosphorous oxybromide in 1.7 mL of CHCl₃ was stirred at 50° C. under a slow stream of Ar for 1.5 h, then allowed to cool to rt overnight. The reaction mixture was diluted with CHCl₃ and ice water, basified with NH₄OH, and extracted with CHCl₃. The combined organic layers were dried over Na₂SO₄, treated with activated carbon, filtered and concentrated to give 7-4 as an orange colored solid: $^1$H NMR (CDCl₃) δ 7.06 (s, 1H), 4.77 (s, 2H), 4.27 (q, 2H, 7.2 Hz), 2.24 (s, 3H), 1.31 (t, 3H, 7.2 Hz).

Step E: 2,2-Difluoro-2-phenylacetamide (7-5)

To a stirred 2.62 mL (16.5 mmol) portion of ethyl benzoylformate was added 5.32 g (33 mmol) of diethylamino sulfurtrifluoride in one portion. After stirring for 4 h at rt under a slow stream of Ar, the contents of the flask were carfully poured into ice-water and extracted with two portions of CH₂Cl₂, the combined organic layers washed with brine, dried over MgSO4 and the solvents evaporated to give 3.0 g of a pale amber oil. This oil was dissolved in 25 mL of absolute ethanol and saturated with gaseous ammonia for 0.5 h. The pressure flask was stoppered and allowed to stand overnight. The solvents were removed to give a yellow solid that was crystallized by dissolving in 7 mL of warm EtOAc, and adding 25 mL of hot hexane. After cooling for several hours, the crystals were collected by filtration, washed with 1:4 EtOAc-hexane and dried to give 7-5 as a tan solid: $^1$H NMR CDCl₃) δ 7.6–7.67 (m, 2H), 7.4–7.54 (m, 3H), 6.37 (br s, 1H), 5.79 (br s, 1H).

Step F: 2.2-Difluoro-2-phenylethvlamine (7-6)

Following the procedures described in Middleton and Bingham J. Org. Chem., 1980, 45, 2883, 500 mg portion of 7-5 (4.826 mmol) was dissolved in 25 ml of THF and cooled to 0° C. via ice bath. To this stirred solution was added 30 ml (30 mmol) of 1M Borane•THF complex dropwise over ten mintes via syringe. The reaction mixture was aged until the ice bath expired. Upon expiration of the ice bath, the reaction mixture was heated to 70° C. overnight. The reaction mixture was diluted with water and concentrated in vacuo. The residue was diluted with chloroform and washed with 10% sodium carbonate. Three chloroform extractions were performed on the aqueous layer. The organic layers were combined, dried (sodium sulfate), and concentrated in vacuo to give 450 mg of a yellow oil. The oil was purified using a 30mm column, 5 inches of silica gel, and a 1:1 ethyl acetate to hexane solvent system to give 7-6 (Wade and Kheribet J. Org. Chem, 1980, 45, 5333) as a yellow oil: H$^1$ NMR CDCl₃): δ 3.15 (t, 2H, 14.6 Hz), 7.4–7.49 (m, 5H).

Step G: 3-(2,2-Difluoro-2-phenylethylamino)-1-(ethoxycarbonylmethyl)-6-methylpyrazinone (7-7)

To a stirred suspension of 507 mg (1.843mmol) of 7-4 in 10 ml of toluene was added 578 mg (3.68 mmol) of 7-6 via pipet. The reaction mixture was heated to 110° C. overnight. The solution was allowed to cool to room temperature and ethyl acetate was added. The diluted reaction mixture was washed with 10% hydrochloric acid. Three ethyl acetate extractions were performed on the aqueous layer. The organic layers were combined, dried (sodium sulfate), and concentrated in vacuo to give 745 mg of an off white solid. The solid was purified using a 40 mm column, 6 inches of silica gel and a 1:1 ethyl acetate/hexane solvent system to give 7-7 as a colorless solid: H$^1$ NMR CDCl₃): δ 1.25 (t, 3H, 6.2 Hz), 2.1 (s, 3H), 4.0–4.1 (m, 2H), 4.25 (q, 2H, 7.1 Hz), 4.72 (s, 2H), 6.15 (s 1H), 6.68 (s, 1H) 7.4–7.6 (m, 3H), 7.6–7.8 (m, 2H).

Step H: 3-(2,2-Difluoro-2-phenylethylamino)-1-(2-amino-6-methyl-5-methylenecarboxamidomethylpyridinyl)-6-methylpyrazinone bis-TFA salt (7-8)

A solution of 350 mg (1.086 mmol) of 7-7 in 381 mg (1.085 mmol) in 20 ml of methanol and 5 ml of water was treated with a 10 molar excess of potassium hydroxide, and heated overnight at 40° C. Acidification with 10% hydrochloric acid to a pH of 3 followed by concentration in vacuo gave 350 mg of 3-(2,2-difluoro-2-phenylethylamino-1-(carboxymethyl)-6-methyl pyrazinone. This material was treated with 147 mg (1.09 mmol) of HOBT, and 228 mg (1.09 mmol) of 2-amino-5-methylamino-6-methylpyridine dihydrochloride in 5 mL of DMF. To this stirred solution was added 208 mg (1.09 mmol) of EDC followed by 2 mL (14.2 mmol) of triethylamine. The reaction mixture was heated to 40° C. and aged overnight. The crude reaction mixture was concentrated in vacuo. The reaction mixture was diluted with chloroform and was washed with 10% sodium carbonate. Three chloroform extractions were performed on the aqueous layer. The organic layers were combined, dried (sodium sulfate), and concentrated in vacuo to give an off white solid. The crude product was purified by preparatory HPLC and the pure fractions were concentrated and lyophilized to give 7-8 as a white solid: $H^1$ NMR (CD$_3$OD): δ 2.16 (s, 3H), 2.51 (s, 3H), 4.1 (t, 2H, 14.5 Hz), 4.3 (s, 2H), 4.72 (s, 2H), 6.65 (s, 1H), 6.7 (d, 1H, 9.1 Hz), 7.4–7.5 (m, 3H), 7.5–7.7 (m, 2H), 7.84 (d, 1H, 9.1 Hz), 8.8 (br s, 1H).

EXAMPLE 8

Preparation of 3-[2-(3-Fluorophenyl)ethylamino]-1-(2-amino-6-methyl-5-methylenecarboxamidomethylpyridinyl)-6-methylpyrazinone bis-TFA salt (8-3)

Step A: 3-[2-(3-Fluorophenyl)ethylamino]-1-(benzyloxycarbonylmethyl)-5-chloro-6-methylpyrazinone (8-1)

A 256 mg (1.834 mmol) portion of 2-(3-fluorophenyl) ethyl-amine was dissolved in 25 ml of toluene. While stirring, 300 mg (0.917 mmol) of 3,5-dichloro-6-methyl-1-(benzyloxycarbonylmethyl)-pyrazinone was added. The reaction mixture was refluxed overnight. The crude reaction mixture was concentrated in vacuo, diluted with chloroform, and transferred to a seperatory funnel where it was washed with 10% sodium bicarbonate solution. Three chloroform extractions were performed on the aqueous layer. The organic layers were combined, dried over sodium sulfate, and concentrated in vacuo to give a crude yellow solid. The solid was purified using a 30 mm column, 6 inches of silica gel and a 1:1 ethyl acetate to hexane solvent system to give 8-1 as a colorless solid: H NMR (CDCl$_3$): δ 2.21 (s, 3H), 2.92 (t, 2H, 7.1 Hz), 3.65 (q, 2H, 6.7 Hz), 4.70 (d, 2H, 5.7 Hz), 4.79 (s, 2H), 6.09 (br s, 1H), 6.92–6.95 (m, 2H), 6.95(d, 1H, 7.5 Hz), 7.2–7.3 (m, 1H), 7.3–7.37 (m, 5H).

Step B: 3-[2-(3-Fluorophenyl)ethylamino]-1-carboxymethyl-6-methylpyrazinone (8-2)

A 162 mg (0.377 8 mmol) portion of 8-1 was suspended in 16 ml of methanol. While stirring, 237 mg (4.23 mmol) of potassium hydroxide was added as a solution in 12 ml of distilled water. The reaction was aged over night at 40° C. The reaction mixture was transferred to a hydrogenation vessel where 130 mg of 10% palladium/carbon was added. The mixture was shaken under hydrogen at 60 psi overnight. The reaction mixture was filtered through celite and the filtrate concentrated in vacuo to give an off white solid which was treated with 10% hydrochloric acid to a pH of 3 and concentrated to give 8-2 which was used directly in the next step.

Step C: 3-[2-(3-Fluorophenyl)ethylarnino]-1-(2-amino-6-methyl-5-methylenecarboxamidomethylpyridinyl)-6-methylpyrazinone bis-TFA salt (8-3)

To a stirred solution of crude 8-2 from Step B, HOBT 297 mg (2.2 mmol), and 301 mg (2.2 mmuHol) of 2-amino-5-methylamino-6-methylpyrdine dihydrochioride in 8 ml of DMF was added 421 mg (2.2 mmol) of EDC followed by 1 ml (73 mmol) of triethylamine. The reaction was aged for 48 hours at room temperature. The crude reaction mixture was concentrated in vacuo, diluted with chloroform, and washed with 10% sodium carbonate solution. Three chloroform extractions were performed on the aqueous layer. The organic layers were combined, dried over sodium sulfate and concentrated in vacuo to give a yellow solid. The solid was dissolved in a 4:1 THF/water and purified by preparatory HPLC. The desired fraction s were combined, concentrated, 8-3

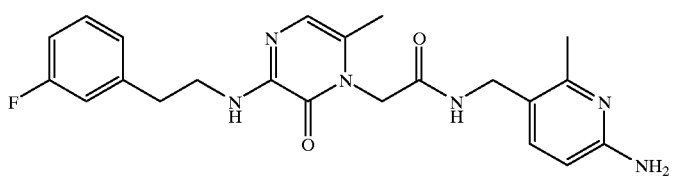

and lyopholized to give 8-3 as a white solid: $H^1$ NMR (CD$_3$OD): δ 2.18 (s, 3H), 2.51 (s, 3H), 3.31 (t, 2H, 7.4 Hz), 3.66 (t, 2H, 7.5 Hz), 4.31 (d, 1H, 9.15 Hz), 6.94–6.96 (m, 1 H), 6.9–7.1 (m, 2H), 7.29–7.33 (m, 1H), 7.83 (d, 2H, 9.0 Hz), 8.8 (br s, 1H).

EXAMPLE 9

Preparation of 3-[2-(5,6 cyclopenteno-2-pyridyl) ethyl]-1-(2-arnino-6-methyl-5-methylenecarboxamidomethylpyridinyl)-6-methylpyrazinone tris-TFA salt (9-9)

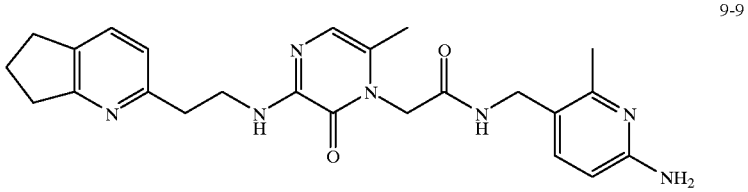

9-9

Step A: 2,3-Cyclopentenopyridine-N-oxide (9-1)

To a solution of 4 g (33.56 mmol) of 2,3-cyclopentenopyridine in 60 ml of methylene chloride was added 8.4 g (100 mmol) of sodium bicarbonate in 60 ml of water. The stirred two phase reaction mixture was cooled to 0° C. and 11.58 g (40 mmol) of 55–65% m-chloroperoxybenzoic acid was added in four portions over 5 minutes. The reaction was aged overnight allowing the ice bath to expire. The reaction mixture was diluted with methylene chloride and was washed with 10% sodium sulfate solution. The aqueous layer was extracted three times with methylene chloride. The organic layers were combined, dried over sodium sulfate, and concentrated under reduced pressure to give a white solid which was purified using column chromatography ( silica gel, 5:95 methanol/chloroform) to give 9-1 as a colorless solid: $H^1$ NMR CDCl$_3$): δ 2.1–2.2 (m, 2H), 3.0 (t, 2H, 7.5Hz), 3.15 (t, 2H, 7.7 Hz), 7.0–7.2 (m, 2H), 8.0 (d, 1H, 6.22 Hz).

Step B: 2-Cyano-5,6-cyclopentenopyridine (9-2)

A solution of 2.0 g (14.8 mmol) of 9-1 in 30 ml of methylene chloride was added to 1.857g (18.72 mmol) of trimethylsilyl cyanide. To this stirred solution was added 2.013 g (18.72 mmol) of dimethyl carbamyl chloride in 3.5 ml of methylene chloride via addition funnel. The reaction was aged overnight. 10% Sodium carbonate solution was added and the reaction mixture was stirred for 10 minutes and then was extracted with methylene chloride. The aqueous layer was extracted three more times with methylene chloride. The organic layers were combined, dried (magnesium sulfate), and concentrated in vacuo to give 3.70 g of a dark semi-solid. The mixture was purified by column chromatography (silica gel, 1:9 ethyl acetate/chloroform) to give 9-2 as a white solid: $H^1$ NMR CDCl$_3$): δ 2.1–2.2 (m, 2H), 3.0–3.15 (m, 4H), 7.43 (d, 1H, 7.7 Hz), 7.60 (d, 1H, 7.7 Hz).

Step C: 5,6-Cyclopentenopyridine-2-carboxylic acid (9-3)

A 1.4 g (9.7 mmol) portion of 9-2 was dissolved in 40 ml of concentrated hydrochloric acid and refluxed for 1.5 hours. The reaction mixture was concentrated in vacuo to give 9-3 as a white solid which was used directly in the next reaction.

Step D: Methyl-5,6-cyclopentenopyridine-2-carboxylate (9-4)

A suspension of 9-3 from Step C in 20 ml of methanol and 60 ml of methylene chloride was titrated with trimethyl silyl diazomethane until a yellow solution resulted. The solution was concentrated in vacuo to give 9-4 as a yellow solid: $H^1$ NMR CDCl$_3$): δ 2.1–2.39 (m, 2H), 2.95 (t, 2H, 7.5 Hz), 3.05 (t, 2H, 7.7), 4.0 (s, 3H), 6.9 (d, 1H, 7.7 Hz), 7.9 (d, 1H, 7.7 Hz).

Step E: 2-Hydroxymethyl-5,6-cyclopentenopyridine (9-5)

A solution of 1.8 g (9.7 mmol) of 9-4 in 45 ml of THF was cooled to 0° C., and a solution of IM lithium aluminum hydride in THF (10.5 ml, 10.5 mmol) was added dropwise via syringe over 15 minutes. The reaction was aged for 1 hour. The reaction mixture was cooled to 0° C. and 2 mL of water, 6 mL of 15% sodium hydroxide solution, and 2 mL more of water were added sequentially. The resulting mixture was filtered and concentrated in vacuo to give 9-5 as a yellow solid: $H^1$ NMR CDCl$_3$): δ 2.1–2.17 (m, 2H), 2.3 (t, 2H, 7.5 Hz), 3.05 (t, 2H, 7.7 Hz), 4.64 (s, 2H), 7.19 (d, 1H, 7.7 Hz), 7.50 (d, 1H, 7.7 Hz).

Step F: 2-Chloromethyl-5,6-cyclonentenopyridine(9-6)

To a stirred solution of 1.4 g (9.7 mmol) of 9-5 in 40 mL of methylene chloride was added 16.7g (141 mmol) of thionyl chloride. The reaction was aged for 1 hour and was concentrated in vacuo. The resulting residue was dissolved in methylene chloride and washed with 1M sodium bicarbonate solution. Three methylene chloride extractions were performed on the aqueous layer. The organic layers were combined, dried (magnesium sulfate), and concentrated to give 9-6 as a dark oil: $H^1$ NMR CDCl$_3$): δ 2.1–2.17 (m, 2H), 2.93 (t, 2H, 7.5 Hz), 3.03 (t, 2H, 7.7 Hz), 4.65 (s, 2H), 7.2 (d, 1H, 7.7 Hz), 7.5 (d, 1H, 7.7 Hz).

Step G: 2-Cyanomethyl-5,6-cyclopentenopyridine (9-7)

To a stirred solution of 1.06 g (6.32 mmol) of 9-6 in 20 ml of DMF was added 1.23 g (19 mmol) of potassium cyanide. The reaction was aged overnight. The crude reaction mixture was concentrated and the residue dissolved in methylene chloride. The solution was washed with 10% sodium carbonate solution. Three methylene chloride extractions were performed on the aqueous layer. The organic layers were combined, dried (magnesium sulfate), and concentrated to give 9-7 as a dark oil: ms (FAB) (M+1)$^+$ 159; $H^1$ NMR CDCl$_3$): δ 2.1–2.17 (m, 2H), 2.93 (t, 2H, 6.2 Hz), 3.0 (t, 2H, 7.7 Hz), 3.88 (s, 2H), 7.15 (d, 1H, 7.7 Hz), 7.5 (d, 1H, 7.5 Hz).

Step H: 2-(5,6-cyclopenteno-2-pyridyl)ethylamine (9-8)

To a solution of 381 mg (2.41 mmol) of 9-8 in methanol (12 ml) and acetic acid (3 ml) was added 381 mg of 10% palladium on carbon. The mixture was shaken on a parr hydrogenator at 60 psi overnight. The mixture was filtered through cellite and concentrated in vacuo. The residue was dissolved in chloroform and was washed with 1M potassium hydroxide solution. Three chloroform extractions were performed on the aqueous layer. The organic layers were combined, dried (sodium sulfate), and concentrated to give 9-8 as an amber oil: $H^1$ NMR CDCl$_3$): δ 2.1–2.2 (m, 2H), 2.8 (t, 2H, 7.7 Hz), 3.9 (t, 2H, 7.5 Hz), 3.1 (t, 2H 6.6 Hz), 3.2 (t, 2H, 6.8 Hz), 3.6 (br s, 2H), 6.9 (d, 1H, 7.9 Hz), 7.4 (d, 1H, 7.5 Hz).

Step I: 3-[$^2$-(5,6-Cyclopenteno-2-pyridyl)ethyl]-1-(2-amino-6-methyl-5-methylenecarboxamidomethylpyridinyl)-6-methylpyrazinone tris-TFA salt (9-9)

9-9 was synthesized using the general procedure of Example 8 to give 9-9 as a white solid: $H^1$ NMR (CD$_3$OD): 2.18 (s, 3H), 2.3 (m, 2H), 2.5 (s, 3H), 3.1 (t, 2H, 7.3 Hz), 3.2 (t, 3H, 7.9 Hz), 3.3–3.45 (m, 4H), 4.3 (s, 2H), 4.8 (s, 2H), 6.7 (s, 1H), 6.8 (d, 1H, 9.0 Hz), 7.6 (d, 1H 7.9 Hz), 7.8 (d, 1H, 9.0 Hz), 8.2 (d, 1H, 7.9 Hz).

EXAMPLE 10

Preparation of 3-{2-[6-(1,4-Benzodioxan)]ethylamino}-6-methyl-1-(2-amino-6-methyl-5-methylenecarboxamidomethylpyridinyl)-pyrazinone (10-5)

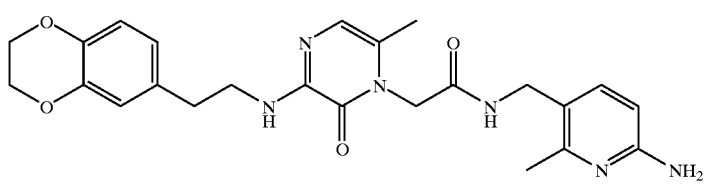

10-5

Step A: 6-(1,4-Benzodioxan)-2-nitroethene (10-1)

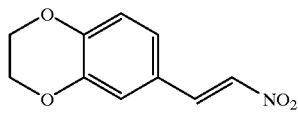

To a solution of 1,4-benzodioxan-6-carboxaldehyde (3.00 g, 18.27 mmol) in N-methyl morpholine (70 mL) was added anhydrous nitromethane (5.58 g, 91.37 mmol), anhydrous potassium fluoride (0.49 g, 8.42 mmol) and anhydrous 18-crown-6 (0.122 g). After 1 h acetic anhydride (5.59 g, 54.81 mmol) and a catalytic amount of DMAP was added. The reaction was poured into ice water (100 mL) after 2.5 hr and extracted with methylene chloride (2×100 mL). The organic layer was washed with water (1×50 mL), brine (1×50 mL) and dried over MgSO$_4$. The solution was filtered, the solvent was removed in vacuo and the oil was purified by flash column chromatography (40×150 mm column of SiO$_2$, CH$_2$Cl$_2$/Hex 1:1) to afford 10-1: $^1$H NMR (400 MHz, CDCl$_3$) δ 4.27-4.33 (m, 4H), 6.09 (dd, J=7.1 and 1.8 Hz, 1H), 7.05–7.07 (m, 2H), 7.48 (d, J=13.5 Hz, 1H), 7.90 (d, J=13.5 Hz, 1H).

Step B: 2-[6-(1,4-benzodioxan)]ethylamine (10-2)

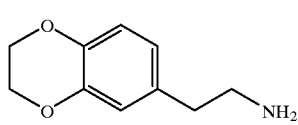

To a solution of 10-1 (1.30 g, 6.27 mmol) dissolved in THF (12 mL), cooled to 0° C., was added borane THF complex (25.1 mL, 1.0 M in THF, 25.1 mmol) dropwise. The ice bath was removed and NaBH$_4$ (0.119 g, 3.14 mmol) was added and the reaction was warmed to 65° C. After 24 h the reaction was poured into ice (100 mL), acidified to pH 2 with 3 N HCl and warmed to 65° C. for 2 h. The mixture was cooled to RT, the pH was adjusted to 8 with aqueous NaOH (1N) and the solvent was removed in vacuo. The aqueous layer was extracted with methylene chloride (3×75 mL) and the combined organic layer was washed with water (2×50 mL), brine (1×50 mL), dried over MgSO$_4$, filtered, concentrated in vacuo. The oil 10-2 was used directly in the next step: $^1$H NMR (400 MHz, CDCl$_3$) δ 2.63 (t, J=6.8 Hz, 2H), 2.92 (t, J=6.8 Hz, 2H), 4.22–4.26 (m, 4H), 6.65–6.73 (m, 2H), 6.79 (d, J=8.2 Hz, 1H).

Step C: 3-{2-[6-(1,4-Benzodioxan)]ethylamino}-5-chloro-6-methyl-1-(benzyloxycarbonylmethyl)-pyrazinone (10-3)

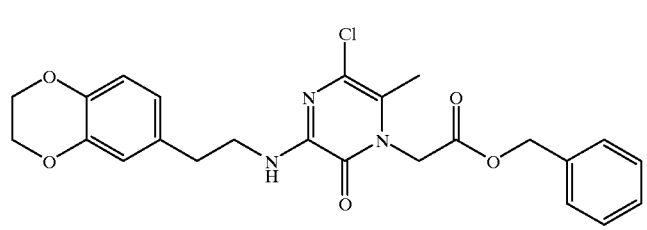

10-3

10-2 (0.295 g, 1.65 mmol) was added to a stirred mixture of 1-benzyloxycarbonylmethyl-3,5-dichloro-6-methylpyrazinone (0.27 g, 0.825 mmol) and triethylamine (0.1 g, 0.99 mmol) in dioxane (7 mL) and the resulting mixture was heated 95° C. under argon. After 16 h the reaction was cooled, the volatiles were removed in vacuo and the oil was purified by flash column chromatography (20×150 mm column of SiO$_2$, CH$_2$Cl$_2$/EtOAc 95:5) to afford 10-3: $^1$H NMR (CDCl$_3$): δ 2.21 (s, 3H, CH$_3$), 2.81 (t, J=7.1 Hz, 2H, PhCH$_2$), 3.62 (q, J=6.8 Hz, 2H, CH$_2$NH), 4.24 (s, 4H, OCH$_2$CH$_2$O), 4.78 (s, 2H, CH$_2$), 5.21 (s, 2H, CH$_2$), 6.08 (br t, 1H, NH), 6.68 (d, J=8.6 Hz, 1H, CH), 6.78 (s, 1H, CH), 6.79 (d, J=8.1Hz, CH), 7.34–7.38 (m, 5H, Ph).

Step D: 3-{2-[6-(1,4-Benzodioxan)]ethylaminol}-6-methyl-1-carboxymethylpyrazinone (10-4)

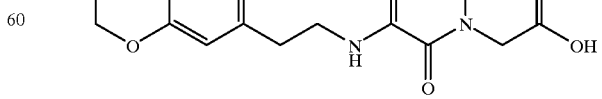

10-4

To a solution of 10-3 (0.36 g, 0.766 mmol) in ethanol (8 mL) under argon was added water (8 mL) and KOH (0.172 g, 3.06 mmol). The mixture was degassed with argon, 10%

Pd/C (0.3 g) was added and the mixture was stirred under a hydrogen filled balloon. After 16 h the reaction was degassed with argon, filtered, and the volatiles were evaporated in vacuo. The residue 10-4 was used directly in the next step.

Step E: 3-{2-[6-(1,4-Benzodioxan)]ethylamino}-6-methyl-1-(2-amino-6-methyl-5-methylcarboxamidomethylpyridinyl)-pyrazinone (10-5)

EDC·HCl (0.154 g, 0.804 mmol) was added to a stirred mixture of 10-4 (0.264 g, 0.766 mmol), 2-amino-5-aminomethyl-6-methylpyridine dihydrochloride (0.177 g, 0.843 mmol), HOBt·H$_2$O (0.108 g, 0.804 mmol) and triethylamine (0.31 g, 3.06 mmol) in dry DMF (5 mL). After 16 h, the volatiles were evaporated in vacuo and the residue was partitioned between ethyl acetate and 1 M HCl solution. The aqueous layer was adjusted to pH 10 with saturated sodium carbonate solution and the precipitate was collected by filtration, washing with water and ethanol to give 10-5 as the free base: MS (FAB) 465 (M+1)$^+$; $^1$H NMR (DMSO-d$_6$): δ 2.22 (s, 3H, CH$_3$), 2.49 (s, 3H, CH$_3$), 2.91 (t, J=7.7 Hz, 2H, PhCH$_2$), 3.41 (q, J=6.4 Hz, 2H, CH$_2$NH), 4.10 (d, J=5.1 Hz, 2H, CONHCH$_2$), 4.19 (s, 4H, OCH$_2$CH$_2$O), 4.57 (s, 2H, CH$_2$CO), 5.73 (s, 2H, NH$_2$), 6.22 (d, J=8.1 Hz, 1H, CH), 6.62–6.77 (m, 5H, CH, CH$_2$NH), 8.41 (br t, J=5.5 Hz, 1H, CONH).

EXAMPLE 11
Preparation of 3-[2-(3,4-dimethoxyphenyl)ethylamino]-6-methyl-1-(2-amino-6-methyl-5-methylenecarboxamidomethylpyridinyl)-pyrazinone (11-1)

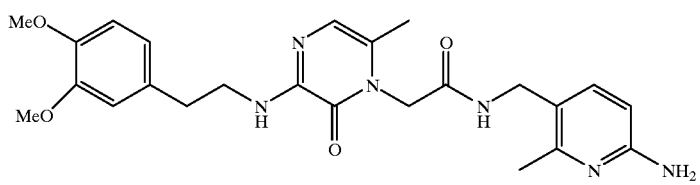

Substituting 2-(3,4-dimethoxyphenyl)-ethylamine for 10-2 in Step C, Example 10 resulted in the preparation of 11-1. MS (FAB) 467 (M+1)$^+$; $^1$H NMR (DMSO-d$_6$): δ 2.02 (s, 3H, CH$_3$), 2.23 (s, 3H, CH$_3$), 2.77 (t, J=7.2 Hz, 2H, PhCH$_9$), 3.46 (q, J=6.6 Hz, 2H, CH$_2$NH), 3.71 (s, 3H, CH$_3$O), 3.72 (s, 3H, CH$_3$O), 4.10 (d, J×5.5 Hz, 2H, CONHCH$_2$), 4.58 (s, 2H, NCH$_2$CO), 5.71 (s, 2H, N$_2$), 6.22 (d, J=8.1 Hz, 1H, CH), 6.63 (s, 1H, 8.1 Hz, 1H, CH), 6.71–6.73 (m, 2H, CH, NH), 6.81 (d, J=1.8 Hz, 1H, CH), 6.85 (d, J=8.1 Hz, 1H, CH), 8.40 (br t, J=4.9 Hz, 1H, CONH).

EXAMPLE 12
Preparation of 3-[1-(3,4-(methylenedioxy)phenyl)-1-cyclopropane-methylamino)]-6-methyl-1-(2-amino-6-methyl-5-methylene-carboxamidomethylpyridinyl)-pyrazinone dihydrochloride (12-3)

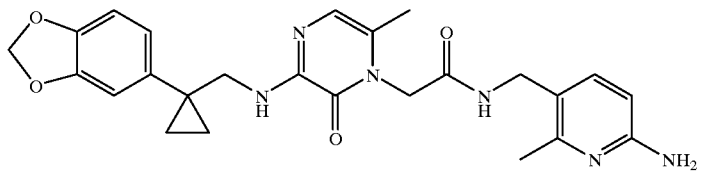

Step A: 1-[3,4-(methylenedioxy)phenyl]-1-cyclopropane-methylamine (12-1)

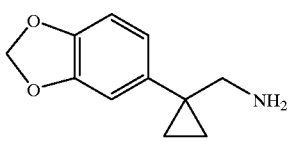

To a solution of 1-[3,4-(methylenedioxy)phenyl]-1-cyclopropanecarbonitrile (1.1 g, 6.2 mmol), prepared following the procedure of Stevens and DuPree (*J. Chem. Soc., Chem. Commun.* 1970, 23, 1585), in 25 mL of anhydrous diethyl ether cooled to 0° C. under an atmosphere of argon was added LiAlH$_4$ (0.47 g, 12.38 mmol) portionwise. After 3 h the reaction was quenched with the addition of water (0.5 mL), 15% NaOH (0.5 mL) and then water (1.5 mL). The solid was filtered and washed with ether and the filtrate was concentrated in vacuo to provide 12-1: $^1$H NMR (CDCl$_3$): δ 0.67–0.71 (m, 2H, CH$_2$), 0.75–0.79 (m, 2H, CH$_2$), 1.78 (v br s, 2H, CH$_2$NH$_2$), 2.70 (s, 2H, CH$_2$NH$_2$), 5.93 (s, 2H, OCH$_2$O), 6.72–6.83 (m, 3H, CH).

Step B: 3-{1-[3,4-(methylenedioxy)phenyl]-1-cyclopropane-methylamino}-5-chloro-6-methyl-1-(benzyloxycarbonylmethyl)-pyrazinone (12-2)

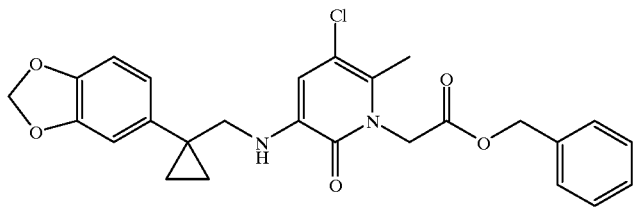

12-2

Substituting 12-1 for 10-2 in Step C, Example 10 resulted in the preparation of 12-2: $^1$H NMR (CDC$_{13}$): δ 0.86–0.89 (m, 4H, CH$_2$CH$_2$), 2.19 (s, 3H, CH$_3$), 3.50 (d, J=5.5 Hz, 2H, CH$_2$NH), 4.76 (s, 2H, NCH$_2$CO), 5.21 (s, 2H, OCH$_2$),5.91 (s, 2H, OCH$_2$O), 6.10 (br t, 1H, NH), 6.71(dd, J=0.4, and 7.9 Hz, 1H, CH), 6.79–6.83 (m, 2H, CH), 7.27–7.38 (m, 5H, Ph).

Step C: 3-{1-[3,4-(methylenedioxy)phenyl]-1-cyclopropane-methylamino}-6-methyl-1-(2-amino-6-methyl-5-methylenecarboxamidomethylpyridinyl)-pyrazinone dihydrochloride (12-3)

To a solution of 12-2 (0.26 g, 0.54 mmol) in ethanol (10 mL) was added a solution of potassium hydroxide (0.121 g, 2.16 mmol) dissolved in water (10 mL). After 3.5 h, Raney nickel (2.0 mL, 50% slurry in water) was added and the reaction was placed under a hydrogen balloon. After 18 h, the reaction mixture was filtered through celite, washed with ethanol and concentrated in vaeuo to provide crude carboxylic acid which used directly in the next step. EDC•HCl (0.109 g, 0.567 mmol) was added to a stirred mixture of carboxylic acid (from above), 2-amino-5-aminomethyl-6-methylpyridine dihydrochloride (0.119 g, 0.567 mmol), HOBt•H$_2$O (0.076 g, 0.567 mmol) and triethylamine (0.22 g, 2.16 mmol) in dry DMF (5 mL). After 16 h, the volatiles were evaporated in vacuo and the residue was partitioned between ethyl acetate and 1 M HCl solution. The aqueous layer was adjusted to pH 10 with saturated sodium carbonate solution and the precipitate was collected by filtration, washing with water and ethanol to give the title compound as the free base. This was dissolved in ethanolic HCl (5 mL) and concentrated to a solid which was titrated with methylene chloride and filtered to provide 12-3: MS (FAB) 477 (M+1)$^+$; $^1$H NMR (DMSO-d$_6$): δ 1.25 (dd, J=4.6 and 5.8 Hz, 2H, CH$_2$), 1.43 (dd, J=4.4 and 5.7 Hz, 2H, CH$_2$), 2.57 (s, 3H, CH$_3$), 2.95 (s, 3H, CH$_3$), 4.17 (br s, 2H, CH$_2$NH), 4.65 (d, J=5.5 Hz, 2H, CONHCH$_2$), 5.11 (s, 2H, NCH$_2$CO), 6.46 (s, 2H, OCH$_2$O), 7.10 (s, 1H, CH), 7.27–7.34 (m, 3H, CH), 7.46 (s, 1H, CH), 8.26 (d, J=9.0 Hz, 1Hz, CH), 8.36 (br s, 2H, NH$_2$), 9.37 (t, 1H, NH).

EXAMPLE 13

Preparation of 3-[2-(3-fluoro-4-methoxyphenyl)ethylamino]-6-methyl-1-(2-amino-6-methyl-5-methylenecarboxamidomethylpyridinyl)-pyrazinone dihydrochloride (13-1)

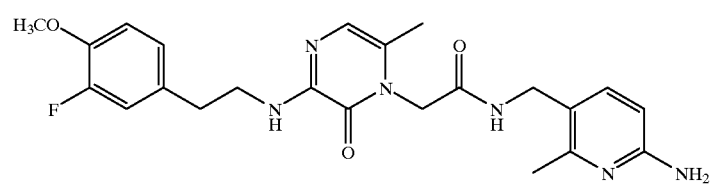

13-1

Starting with 3-fluoro-4-methoxyphenylacetonitrile and following the procedure described in Example 10, 13-1 was prepared. MS (FAB) 455 (M+1)$^+$; mp: >220° C.;

Analysis calculated for C$_{23}$H$_{27}$N$_6$O$_3$F$_1$•2.0 HCl•0.8 CH$_2$Cl$_2$; C,48.01;H,5.18;N,14.12; Found: C,48.10;H, 5.05;N,13.76.

EXAMPLE 14

Preparation of rac-3-(2-phenyl-1-butylamino)-6-methyl-1-(2-amnino-6-methyl-5-methylenecarboxamidomethylpyridinyl)-pyrazinone (14-1)

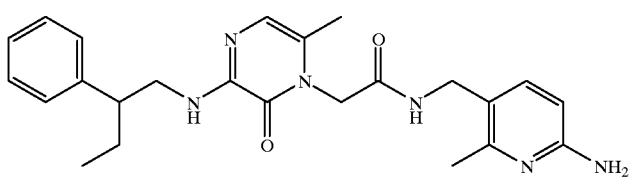

14-1

14-1 was prepared from 1-benzyloxy-carbonylmethyl-3,5-dichloro-6-methylpyrazinone and 1-phenyl-1-cyclopropanemethylamine (which was prepared from 1-phenyl-1-cyclopropanecarbonitrile using the procedure of Example 12, Step A and then using the procedure of Example 5). The final step provided two compounds which were separated by reverse phase preparative HPLC using a gradient elution of water (0.1% TFA) and acetonitrile (0.1% TFA), 95:5 to 55:45 over 1 h. The first compound to elute was 3-(1-phenyl-1-cyclopropanemethylamino)-6-methyl-1-(2-amino-6-methyl-5-methylenecarboxamidomethylpyridinyl)-pyrazinone followed by the titled compound. The appropriate fractions were concentrated and then partitioned between saturated NaHCO$_3$ and EtOAc (20 mL each). The aqueous was extracted with EtOAc (2×15 mL) and the combined organics were dried over MgSO$_4$, filtered and concentrated to a white solid. This was triturated with EtOAc:Hex (5:95), filtered and dried under vacuum to provide 14-1: MS (FAB) 435 (M+1)$^+$.

EXAMPLE 15

Preparation of 3-[2-(6-methyl-2-pyridyl)ethylamino]-6-methyl-1-(2-amino-6-methyl-5-methylenecarboxamidomethylpyridinyl)-pyrazinone dihydrochloride (15-1)

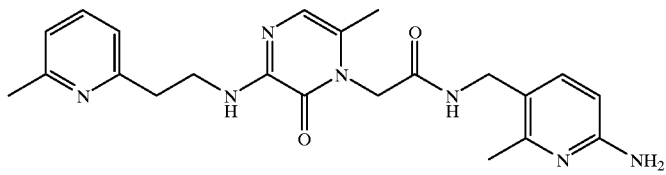

15-1

15-1 was prepared from 1-benzyloxy-carbonylmethyl-3,5-dichloro-6-methylpyrazinone and 2-(6-methyl-2-pyridyl)ethylamine (which was prepared from 6-methylpicolinic acid) using the procedure of Example 10 starting with Step C:

MS (FAB) 422 (M+1)$^+$; mp: >200° C. decomp; Analysis calculated for $C_{22}H_{27}N_7O_2 \cdot 3.7$ HCl•0.45 EtOAc; C,47.95;H,5.80;N,16.45; Found: C,47.64;H,5.92;N,16.24.

EXAMPLE 16

Preparation of 3-(1-cyclopropylmethyl-2-cyclopropylethylamino)-1-(2-amino-6-methyl-5-methylenecarboxamidomethylpyridinyl)-6-methylnyrazin(1H)-2-one (16-5)

Step A: 1,3-Dicyclopropyl-2-pronanol (16-1).

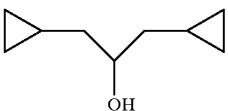

16-1

A stirred solution of 23.5 mL (23.5 mmol) of diethylzinc (1M in hexane) was diluted with 23.5 mL of 1,2-dichloroethane (DCE) and cooled to 0° C. under Ar. A 3.45 mL (47 mmol) portion of chloroiodomethane was added dropwise causing the formation of a precipitate. After stirring for 45 min in the cold, 20 mL of DCE was added, and the mixture stirred for an additional 45 min. To this mixutre was added 763 μL (5.88 mmol) of 1,6-heptadien-4-ol (Aldrich) dropwise. After stirring for 30 min in the cold, the reaction was quenched by the dropwise addition of sat. NH$_4$Cl, and the cold bath was allowed to expire overnight. The reaction mixture was extracted with two portions of ether, and the combined organic layers washed with water, brine, dried over Na$_2$SO$_4$ and the solvents removed to give 16-1 as a pale yellow oil: $^1$H NMR (CDCl$_3$)∂ 3.88–3.77 (m, 1H), 1.84 (d,1H, 3.4 Hz), 1.40 (t, 4H, 6.6 Hz), 0.82–0.70 (m, 2H), 0.56-0.40 (m, 4H), 0.18-0.00 (m, 4H).

Step B: 1,3-Dicyclopropyl-2-Dropyl methanesulfonate (16-2)

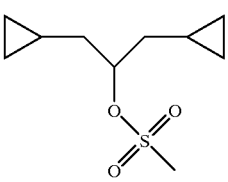

16-2

To a stirred solution of 627 mg(4.47 mmol) of 16-1 and 934 μL (6.7 mmol) of triethylamine in 1.5 mL of CH$_2$Cl$_2$ was added 519 μL (6.7 mmol) of methansulfonyl chloride dropwise under Ar. The resulting exotherm was controlled by placing the flask in an ice bath. After 0.5 h, the reaction mixture was diluted with CHCl₃ and washed with sat NaHCO₃. The aqueous layer was extracted with CHCl₃, and the combined organic layers were washed with sat. NaHCO₃, dried over Na₂SO₄ and treated with activated carbon. Evaporation of the solvents and drying at reduced pressure gave 16-2 as a yellow oil: ¹H NMR (CDCl₃)∂ 4.81 (quin, 1H, 5.6 Hz), 3.03 (s, 3H), 1.79-1.56 (m, 4H), 0.83-0.70 (m, 2H), 0.6-0.45 (m, 4H), 0.20-0.05 (m, 4H).

Step C: 1,3-Dicyclopropyl-2-propyl azide (16-3)

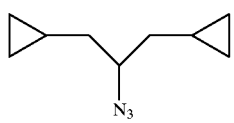

16-3

A solution of 886 mg (4.1 rmmol) of 16-2 and 780 mg (12.0 mmol) of sodium azide in 5 mL of DMF was heated at 50° C. overnight under Ar. After cooling to rt, the reaction mixutre was diluted with water, and extracted with two portions of ether. The combined organic layers were washed twice with water, brine, and dried over Na₂SO₄. Due to the volatility of the product 16-3, this solution was used directly in the next reaction.

Step D: 2-Amino-1,3-dicyclopronylnropane (16-4)

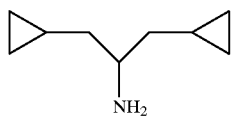

16-4

The stirred solution of 16-3 in approximately 175 mL of ether from the previous step was cooled to 0° C. under Ar, and 759 mg (20 mmol) of lithium aluminum hydride (LAH) was added in small portions. After the addition, the cold batwas removed, and disappearance of azide was monitored by HPLC. The reaction mixture was heated to reflux for 2 h, recooled to 0° C. and an additional portion of 256 mg (6.7 mmol) of LAH was carefully added. The cold bath was allowed to expire, and the reaction mixture allowed to stand for several days. The reaction mixture was cooled to 0° C., and quenched by the sequential dropwise addition of 1 mL H₂O, 1 mL of 15% NaOH, and 3 mL H₂O. The resulting mixture was stirred at rt for 1.5 h, fuirther dried over Na₂SO₄ and evaporated at reduced pressure to give 16-4 as an air sensitive yellow oil: ¹H NMR (CDCl₃)∂ 3.0-2.92 (m, 1H), 1.6 (br s, 2H), 1.41-1.30 (m, 2H), 1.27-1.15 (m, 2H), 0.78-0.65 (m, 2H), 0.55-0.36 (m, 4H), 0.17-0.04 (m, 4H).

Step E: 3-(1-Cyclopropylmethyl-2-cyclopropylethylamino)-1-(2-amino-6-methyl-5-methylenecarboxamidomethylpyridinyl)-6-methylnyrazin (1H)-2-one (16-5)

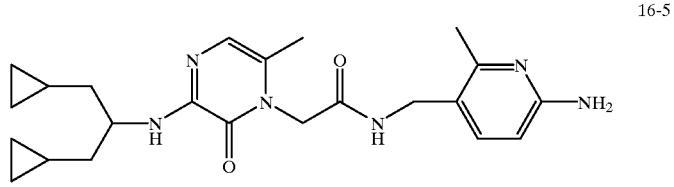

16-5

Using 16-4 from Step D and the methods of Example 7, Steps G and H, the TFA salt of 16-5 was obtained as a pale yellow solid: H¹ NMR (DMSO-d₆): 8.77 (t, 1H), 7.80-7.70 (m, 3H), 6.79 (d, 1H, 9.0 Hz), 6.66 (s, 1H), 4.62 (s, 2H), 4.17 (d, 2H, 5.4 Hz), 4.12-3.97 (m, 1H), 2.42 (s, 3H), 2.07 (s, 3H), 1.63-1.40 (m, 4H, 9.07 Hz), 0.72-0.60 (m, 2H), 0.5-0.3 (m, 4H), 0.15-0.04(m, 4H).

EXAMPLE 17

Preparation of 3-(2,2-difluoro-2-phenylethylamino)-1-(2-amino-3,6-dimethyl-5-methylenecarboxamidomethylpyridinyl)-6-methylpyrazin(1H)-2-one (17-1)

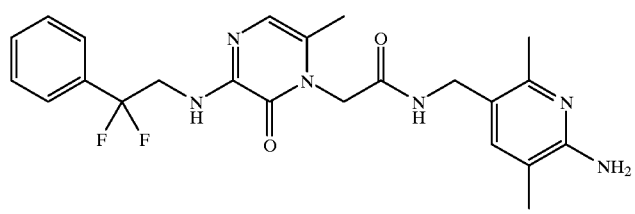

17-1

17-1 was prepared from 3-(2,2-difluoro-2-phenylethylamino-1-(carboxymethyl)-6-methyl pyrazinone and 2-amino-5-aminomethyl-3,6-dimethylpyridine using the procedure of Example 7, Step H: H$^1$ NMR (D$_6$ DMSO): Selected signal at δ 4.06 (dt, 2H, 6.6 and 15.2 Hz, CF$_2$CH$_2$); MS (FAB) 457 (M+1)$^+$.

EXAMPLE 18

Preparation of 3-(2-Cyclobutyl-2,2-difluoroethylamino)-6-methyl-1-(2-amino-6-methyl-5-methylcarboxamidomethylpyridinyl)-pyrazinone dihydrochloride (18-2)

18-2

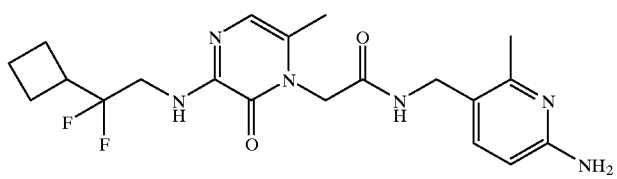

Step A: C 2-Cyclobutvl-2,2-difluoroethvlamine (18-1).

18-1 was prepared as the HCl salt from ethyl-2-oxocyclobutylacetate (which was prepared from cyclobutylmagnesium bromide and diethyloxalate using the procedure of Singh et al. *Org. Prep. Proc. Int.* 1989, 21, 501) using the procedures of Example 7, Steps E and F as a crystalline solid: $^1$H NMR (CD$_3$OD)δ 1.89 (m, 1H), 1.99-2.22 (m, 5H), 2.91 (m, 1H), 3.35 (obscured t, J=15.2 Hz, 2H).

Step B: 3-(2-Cyclobutyl-2,2-difluoroethylamino)-6-methyl-1-(2-amino-6-methyl-5-methylcarboxamidomethylpyridinyl)-pyrazinone dihydrochloride (18-2)

18-2 was prepared as the bis-HCl salt from 18-1 using the procedures of Example 5, Steps C–F as a tan solid: MS (FAB) 421 (M+1)$^+$.

IN VITRO ASSAY FOR DETERMINING PROTEINASE INHIBITION

Assays of human α-thrombin and human trypsin were performed by the methods substantially as described in *Thrombosis Research, Issue* No. 70, page 173 (1993) by S. D. Lewis et al.

The assays were carried out at 25° C. in 0.05 M TRIS buffer pH 7.4, 0.15 M NaCl, 0.1% PEG. Trypsin assays also contained 1 mM CaCl$_2$. In assays wherein rates of hydrolysis of a p-nitroanilide (pna) substrate were determined, a Thermomax 96-well plate reader was used was used to measure (at 405 um) the time dependent appearance of p-nitroaniline. sar-PR-pna was used to assay human α-thrombin (K$_m$=125 µM) and bovine trypsin (K$_m$=125 µM). p-Nitroanilide substrate concentration was determined from measurements of absorbance at 342 nm using an extinction coefficient of 8270 cm$^{-1}$M$^{-1}$.

In certain studies with potent inhibitors (K$_i$<10 nM) where the degree of inhibition of thrombin was high, a more sensitive activity assay was employed. In this assay the rate of thrombin catalyzed hydrolysis of the fluorogenic substrate Z-GPR-afc (K$_m$=27 µM) was determined from the increase in fluorescence at 500 nm (excitation at 400 nm) associated with production of 7-amino-4-trifluoromethyl coumarin. Concentrations of stock solutions of Z-GPR-afc were determined from measurements of absorbance at 380 nm of the 7-amino-4-trifluoromethyl coumarin produced upon complete hydrolysis of an aliquot of the stock solution by thrombin.

Activity assays were performed by diluting a stock solution of substrate at least tenfold to a final concentration ≦0.1 K$_m$ into a solution containing enzyme or enzyme equilibrated with inhibitor. Times required to achieve equilibration between enzyme and inhibitor were determined in control experiments. Initial velocities of product formation in the absence (V$_o$) or presence of inhibitor (V$_i$) were measured. Assuming competitive inhibition, and that unity is negligible compared K$_m$/[S], [I]/e, and [I]/e (where [S], [I], and e respectively represent the total concentrations, of substrate, inhibitor and enzyme), the equilibrium constant (K$_i$) for dissociation of the inhibitor from the enzyme can be obtained from the dependence of V$_o$/V$_i$ on [I] shown in equation 1.

$$V_o/V_i=1+[I]/K_i \qquad (1)$$

The activities shown by this assay indicate that the compounds of the invention are therapeutically useful for treating various conditions in patients suffering from unstable angina, refractory angina, myocardial infarction, transient ischemic attacks, atrial fibrillation, thrombotic stroke, embolic stroke, deep vein thrombosis, disseminated intravascular coagulation, and reocclusion or restenosis of recanalized vessels. The inhibitory activity of compounds of the invention against human thrombin, represented by Ki, is less than 24 nM. These are selective compounds, as evidenced by their inhibitory activity against human trypsin (represented by Ki), which is at least 1000 nM.

Inhibitory activity of compounds of the invention, represented by "*", indicating Ki greater than or equal to 1 nM, or "**", indicating Ki less than 1 nM, and measured using the above assay, is shown above.

EXAMPLE 19

Tablet Preparation

Tablets containing 25.0, 50.0, and 100.0 mg., respectively, of the following active compounds are prepared as illustrated below (compositions A–I). Active I is 3-(2-Cyclobutyl-2,2-difluoroethylamino)-6-methyl-1-(2-amino-6-methyl-5-methylcarboxamidomethylpyridinyl)-pyrazinone dihydrochloride; Active II is 3-[2-(3-Fluorophenethylamino)]-6-methyl-1-(2-amino-3,6-dimethyl-5-methylcarboxamidomethyl-pyridinyl)-pyrazinone_dihydrochloride; Active III is 3-(2-Phenethylamino)-6-methyl-1-(2-amino-3,6-dimethyl-5-methylcarboxamidomethylpyridinyl)-pyrazinone dihydrochloride; and Active IV is 3-(2,2-difluoro-2-phenylethylamino)-1-(2-amino-3,6-dimethyl-5-methylenecarboxamidomethylpyridinyl)-6-methylpyrazin(1H)-2-one.

TABLE FOR DOSES CONTAINING FROM
25–100 MG OF THE ACTIVE COMPOUND

| Component | Amount—mg | | | | | | | | |
|---|---|---|---|---|---|---|---|---|---|
| | A | B | C | D | E | F | G | H | I |
| Active I | 25 | 50 | 100 | — | — | — | — | — | — |
| Active II | — | — | — | 25 | 50 | 100 | — | — | — |
| Active III | — | — | — | — | — | — | 25 | 50 | 100 |
| Microcrystalline cellulose | 37.25 | 100 | 200 | 37.25 | 100 | 200 | 37.25 | 100 | 200 |
| Modified food corn starch | 37.25 | 4.25 | 8.5 | 37.25 | 4.25 | 8.5 | 37.25 | 4.25 | 8.5 |
| Magnesium stearate | 0.5 | 0.75 | 1.5 | 0.5 | 0.75 | 1.5 | 0.5 | 0.75 | 1.5 |

All of the active compound, cellulose, and a portion of the corn starch are mixed and granulated to 10% corn starch paste. The resulting granulation is sieved, dried and blended with the remainder of the corn starch and the magnesium stearate. The resulting granulation is then compressed into tablets containing 25.0, 50.0, and 100.0 mg, respectively, of active ingredient per tablet.

EXAMPLE 20

Tablet Preparation

Exemplary compositions of 3-(2,2-difluoro-2-phenylethylamino)-1-(2-amino-3,6-dimethyl-5-methylenecarboxamidomethylpyridinyl)-6-methylpyrazin (1H)-2-one tablets are shown below:

| Component | 0.25 mg | 2 mg | 10 mg | 50 mg |
|---|---|---|---|---|
| Active IV | 0.500% | 1.000% | 5.000% | 14.29% |
| mannitol | 49.50% | 49.25% | 47.25% | 42.61% |
| microcrystalline cellulose | 49.50% | 49.25% | 47.25% | 42.61% |
| magnesium stearate | 0.500% | 0.500% | 0.500% | 0.500% |

2, 10 and 50 mg tablets were film-coated with an aqueous dispersion of hydroxypropyl cellulose, hydroxypropyl methylcellulose and titanium dioxide, providing a nominal weight gain of 2.4%.

Tablet Preparation via Direct Compression

Active IV, mannitol and microcrystalline cellulose were sieved through mesh screens of specified size (generally 250 to 750 μm) and combined in a suitable blender. The mixture was subsequently blended (typically 15 to 30 min) until the drug was uniformly distributed in the resulting dry powder blend. Magnesium stearate was screened and added to the blender, after which a precompression tablet blend was achieved upon additional mixing (typically 2 to 10 min). The precompression tablet blend was then compacted under an applied force, typically ranging from 0.5 to 2.5 metric tons, sufficient to yield tablets of suitable physical strength with acceptable disintegration times (specifications will vary with the size and potency of the compressed tablet). In the case of the 2, 10 and 50 mg potencies, the tablets were dedusted and film-coated with an aqueous dispersion of water-soluble polymers and pigment.

Tablet Preparation via Dry Granulation

Alternatively, a dry powder blend is compacted under modest forces and remilled to afford granules of specified particle size. The granules are then mixed with magnesium stearate and tabletted as stated above.

EXAMPLE 21

Intravenous Formulations

Intravenous formulations of 3-(2,2-difluoro-2-phenylethylamino)-1-(2-amino-3,6-dimethyl-5-methylenecarboxamidomethylpyridinyl )-6-methylpyrazin (1H)-2-one were prepared according to general intravenous formulation procedures.

| Component | Estimated range |
|---|---|
| Active IV | 0.12–0.61 mg |
| D-glucuronic acid* | 0.5–5 mg |
| Mannitol NF | 50–53 mg |
| 1 N Sodium Hydroxide | q.s. pH 3.9–4.1 |
| Water for injection | q.s. 1.0 mL |

Exemplary compositions A–C are as follows:

| Component | A | B | C |
|---|---|---|---|
| Active IV | 0.61 mg* | 0.30** | 0.15*** |
| D-glucuronic acid* | 1.94 mg | 1.94 mg | 1.94 mg |
| Mannitol NF | 51.2 mg | 51.2 mg | 51.2 mg |
| 1 N Sodium Hydroxide | q.s. pH 4.0 | q.s. pH 4.0 | q.s. pH 4.0 |
| Water for injection | q.s. 1.0 mL | q.s. 1.0 mL | q.s. 1.0 mL |

*0.50 mg free base
**0.25 mg free base
***0.12 mg free base

Various other buffer acids, such as L-lactic acid, acetic acid, citric acid or any pharmaceutically acceptable acid/conjugate base with reasonable buffering capacity in the pH range acceptable for intravenous administration may be substituted for glucuronic acid.

What is claimed is:
1. A compound having the formula:

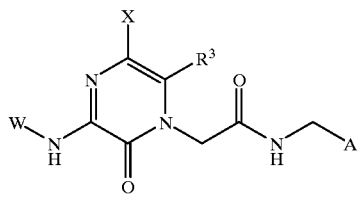

wherein
W is
R²CF₂C(R¹²)2;
R² and R¹⁴ are independently
  phenyl, unsubstituted or substituted with one or more of $C_{1-4}$ alkyl, $C_{1-4}$ alkoxy, halogen, hydroxy, COOH, CONH₂, CH₂OH, CO₂R', where R' is $C_{1-4}$ alkyl, or SO₂NH₂,
  naphthyl,
  biphenyl,
  $C_{1-7}$ alkyl, unsubstituted or substituted with one or more of hydroxy,
    COOH,
    halogen,
    amino,
    phenyl,
    naphthyl,
    $C_{3-7}$ cycloalkyl,
    CF₃,
    N(CH₃)₂,
    —$C_{1-3}$alkylphenyl, or
    —$C_{1-3}$alkylnaphthyl,
  CF₃
  $C_{3-7}$ cycloalkyl, unsubstituted, monosubstituted with halogen, phenyl or naphthyl, or disubstituted with halogen,
  $C_{7-12}$ bicyclic alkyl, or
  $C_{10-16}$ tricyclic alkyl;
R³ is
  hydrogen,
  $C_{1-4}$ alkyl,
  $C_{3-7}$ cycloalkyl, or
  trifluoromethyl;
X is hydrogen or halogen;
A is chosen from one of the following radicals:

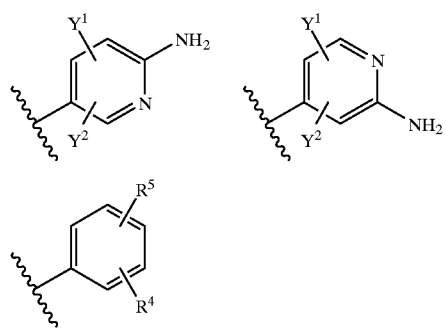

wherein $Y^1$ and $Y^2$ are independently
  hydrogen,
  $C_{1-4}$ alkyl,
  $C_{1-4}$ alkoxy,
  $C_{3-7}$ cycloalkyl,
  halogen, or
  trifluoromethyl;
R⁴ is
  hydrogen,
  $C_{1-4}$ alkyl,
  $C_{1-4}$ alkoxy,
  halogen,
  —OCH₂CF₃,
  —OCH₂CN,
  —COOH,
  —OH,
  —COOR⁶, where R⁶ is $C_{1-4}$alkyl,
  —CONR⁷R⁸, where R⁷ and R⁸ are independently hydrogen or $C_{1-4}$alkyl,
  —(CH₂)₁₋₄OH,
  —CH₂NHC(O)CH₃,
  —CH₂NHC(O)CF₃,
  —CH₂NHSO₂CH₃,
  —SO₂NH₂,
  —(CH₂)₁₋₄SO₂NR⁷R⁸, where R⁷ and R⁸ are as defined above,
  —(CH₂)₁₋₄SO₂R⁶, where R⁶ is as defined above,
  —ZCH₂CO₂H,
  —ZCH₂CO₂CH₃,
  —ZCH₂R¹⁴,
  —ZCH₂NHR¹⁴,
  —ZCH₂CO₂(CH₂)₁₋₃CH₃,
  —Z(CHR⁹)₁₋₃ C(O)NR¹⁰R¹¹,
  wherein
    R⁹ is H or $C_{1-4}$ alkyl,
    R¹⁰ and R¹¹ are independently
      hydrogen,
      $C_{3-7}$ cycloalkyl,
      phenyl,
      naphthyl,
      —(CH₂)₁₋₂ NCH₂CH₃,
      $C_{1-4}$ alkyl unsubstituted or substituted with one or more of:
        hydroxy,
        COOH,
        amino,
        phenyl, or
        naphthyl,
      R¹⁰ and R¹¹ are joined to form a four to seven membered cycloalkyl ring unsubstituted or substituted with hydroxy, amino or phenyl or naphthyl or disubstituted with hydroxy,
  wherein Z is O, S or CH₂;
R⁵ is
  hydrogen,
  halogen ,
  $C_{1-4}$ alkyl,
  $C_{1-4}$ alkoxy,
  CF₃,
  CN, or
  CO₂NH₂; and
R¹² is
  hydrogen,
  phenyl, unsubstituted or substituted with one or more Of $C_{1-4}$ alkyl, $C_{1-4}$ alkoxy, halogen, hydroxy, COOH, CONH₂,
  naphthyl,
  biphenyl,
  $C_{1-4}$ alkyl, unsubstituted or substituted with one or more of hydroxy,
    COOH, amino,
phenyl, or
naphthyl,
CF₃,
$C_{3-7}$ cycloalkyl,
$C_{7-12}$ bicyclic alkyl, or
$C_{10-16}$ tricyclic alkyl or a pharmaceutically acceptable salt thereof.

2. A compound of claim 1, or pharmaceutically acceptable salt thereof, wherein $R^3$ is $C_{1-4}$ alkyl and X is H.

3. A compound of claim 2, or pharmaceutically acceptable salt thereof, wherein A is i) 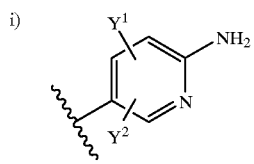

wherein $Y^1$ and $Y^2$ are independently hydrogen, halogen or $C_{1-4}$ alkyl; or ii) 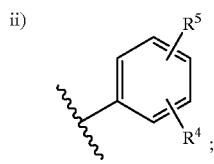

$R^4$ is
hydrogen,
$C_{1-4}$ alkyl,
$C_{1-4}$ alkoxy,
halogen,
—OH,
—OCH₂R¹⁴,
—OCH₂NHR¹⁴,
—O(CH₂)₁₋₃C(O)NR¹⁰R¹¹,
wherein
R¹⁰ and R¹¹ are independently
hydrogen,
$C_{3-7}$ cycloalkyl,
$C_{1-4}$ alkyl substituted with amino, or
R¹⁰ and R¹¹ are joined to form a four to seven membered cycloalkyl ring unsubstituted or substituted with hydroxy, amino or aryl or disubstituted with hydroxy, $R^5$ is
hydrogen,
halogen,
$C_{1-4}$ alkyl, or
CN.

4. A compound of claim 3, or pharmaceutically acceptable salt thereof, wherein $R^2$ is
phenyl, unsubstituted or substituted with one or more of $C_{1-4}$ alkyl, $C_{1-4}$ alkoxy, halogen, hydroxy, or SO₂NH₂,
$C_{3-7}$ cycloalkyl, unsubstituted, monosubstituted or disubstituted with halogen,
CF₃, or
$C_{1-7}$ alkyl, unsubstituted or substituted with halogen or $C_{3-7}$ cycloalkyl; and $R^{12}$ is
hydrogen,
$C_{1-4}$ alkyl, unsubstituted or substituted with one or more of hydroxy,
COOH,
amino,
phenyl,
naphthyl, or
halogen.

5. A compound of claim 4, or pharmaceutically acceptable salt thereof, wherein A is

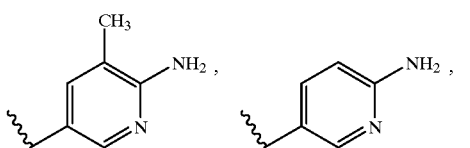

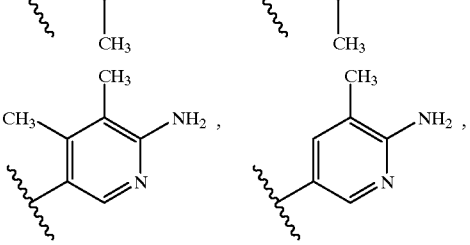

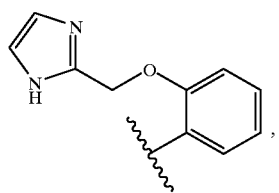,
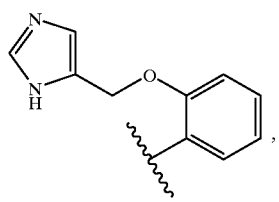,
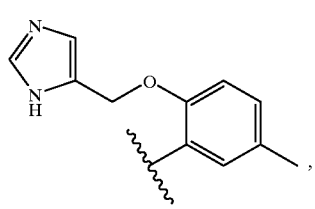,
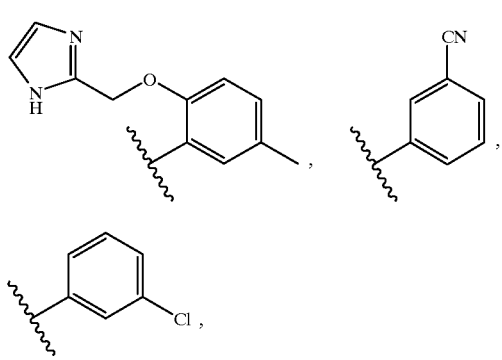,
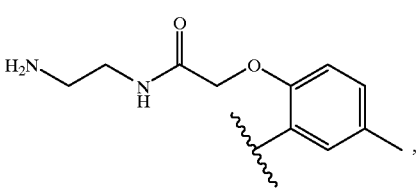,
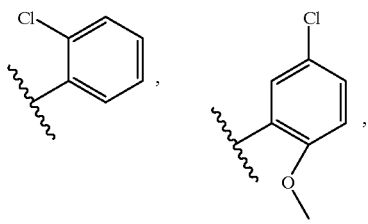,
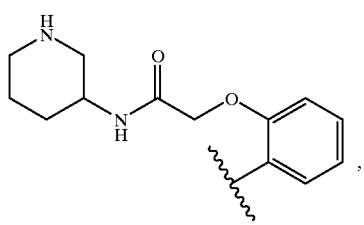,
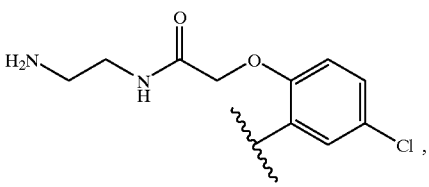,
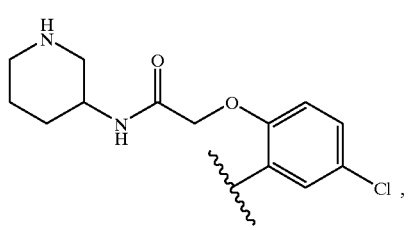,
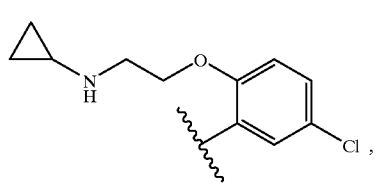,
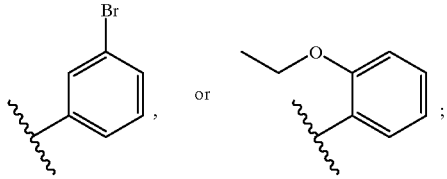;
$R^3$ is $CH_3$, or $CH_2CH_3$; and
W is
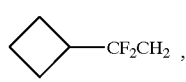,
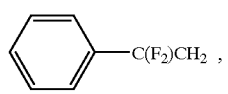,
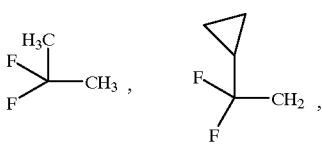.
6. A compound of claim 5 which is selected from the group consisting of

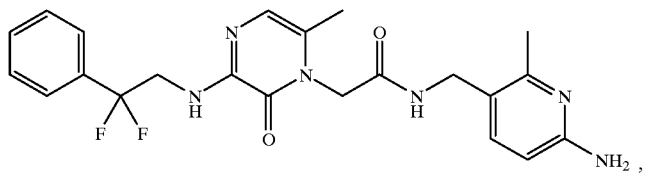

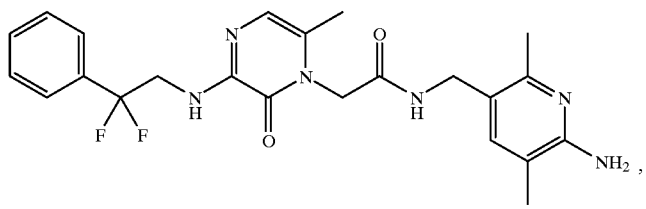

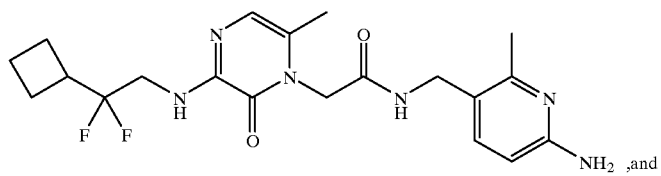

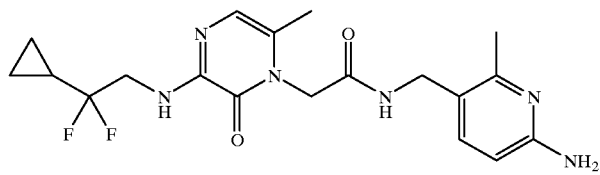

or pharmaceutically acceptable salt thereof.

7. A composition for inhibiting thrombus formation in blood comprising a compound of claim 1 and a pharmaceutically acceptable carrier.

8. A method for inhibiting formation of blood platelet aggregates in blood comprising adding to the blood an effective amount of a composition of claim 7.

9. A method for inhibiting thrombus formation in blood comprising adding to the blood an effective amount of a composition of claim 7.

10. A method for treating or preventing venous thromboembolism and pulmonary embolism in a mammal comprising administering to the mammal an effective amount of a composition of claim 7.

11. A method for treating or preventing deep vein thrombosis in a mammal comprising administering to the mammal an effective amount of a composition of claim 7.

12. A method for treating or preventing cardiogenic thromboembolism in a mammal comprising administering to the mammal an effective amount of a composition of claim 7.

13. A method for treating or preventing thromboembolic stroke in humans and other mammals comprising administering to the mammal an effective amount of a composition of claim 7.

14. A method for treating or preventing thrombosis associated with cancer and cancer chemotherapy in a mammal comprising administering to the mammal an effective amount of a composition of claim 7.

15. A method for treating or preventing unstable angina in a mammal comprising administering to the mammal an effective amount of a composition of claim 7.

* * * * *